US011651494B2

(12) United States Patent
Brown et al.

(10) Patent No.: US 11,651,494 B2
(45) Date of Patent: May 16, 2023

(54) APPARATUSES AND METHODS FOR THREE-DIMENSIONAL DENTAL SEGMENTATION USING DENTAL IMAGE DATA

(71) Applicant: Align Technology, Inc., San Jose, CA (US)

(72) Inventors: Chad C. Brown, Cary, NC (US); Yun Gao, Cary, NC (US); Pavel Agniashvili, Moscow (RU); Avraham Zulti, Modiin (IL); Jonathan Coslovsky, Rehovot (IL); Christopher E. Cramer, Durham, NC (US); Roman Gudchenko, Moscow (RU); Ofer Saphier, Rehovot (IL); Adi Levin, Nes Tziona (IL); Maayan Moshe, Ramat HaSharon (IL); Doron Malka, Tel Aviv (IL)

(73) Assignee: Align Technology, Inc., San Jose, CA (US)

( * ) Notice: Subject to any disclaimer, the term of this patent is extended or adjusted under 35 U.S.C. 154(b) by 302 days.

(21) Appl. No.: 17/013,513

(22) Filed: Sep. 4, 2020

(65) Prior Publication Data
US 2021/0073998 A1    Mar. 11, 2021

Related U.S. Application Data

(60) Provisional application No. 62/896,509, filed on Sep. 5, 2019.

(51) Int. Cl.
*G06T 7/11*    (2017.01)
*G06T 7/00*    (2017.01)
(Continued)

(52) U.S. Cl.
CPC .............. *G06T 7/11* (2017.01); *G06N 3/0454* (2013.01); *G06N 20/00* (2019.01); *G06T 7/0012* (2013.01);
(Continued)

(58) Field of Classification Search
CPC ......... G06T 19/20; G06T 7/11; G06T 17/205; G06F 17/50
(Continued)

(56) References Cited

U.S. PATENT DOCUMENTS 5,975,893 A     11/1999  Chishti et al.
6,227,850 B1     5/2001  Chishti et al.
(Continued)

*Primary Examiner* — Thomas J Lett
(74) *Attorney, Agent, or Firm* — Shay Glenn LLP

(57) ABSTRACT

Methods and apparatuses (including systems and devices), including computer-implemented methods for segmenting, correcting and/or modifying a three-dimensional (3D) model of a subject's oral cavity to determine individual components such as teeth, gingiva, tongue, palate, etc., that may be selective and/or collectively digitally manipulated. In some implementations, artificial intelligence uses libraries of labeled 2D images and 3D dental models to learn how to segment a 3D dental model of a subject's oral cavity using 2D images, height map and/or other data and projection values that relate the 2D images to the 3D model. As noted herein, the dental classes can include a variety of intra-oral and extra-oral objects and can be represented as binary values, discrete values, a continuum of height map data, etc. In some implementations, several dental classes are predicted concurrently.

22 Claims, 17 Drawing Sheets

(51) Int. Cl.
*G06N 3/04* (2023.01)
*G16H 30/20* (2018.01)
*G06N 20/00* (2019.01)
*G06T 17/20* (2006.01)
*G06T 19/20* (2011.01)

(52) U.S. Cl.
CPC ............ *G06T 17/205* (2013.01); *G06T 19/20* (2013.01); *G16H 30/20* (2018.01); *G06T 2207/20081* (2013.01); *G06T 2207/20084* (2013.01); *G06T 2207/30036* (2013.01); *G06T 2210/41* (2013.01); *G06T 2219/2012* (2013.01)

(58) Field of Classification Search
USPC ........................................................ 345/419
See application file for complete search history.

(56) References Cited

U.S. PATENT DOCUMENTS

| | | |
|---|---|---|
| 6,227,851 B1 | 5/2001 | Chishti et al. |
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,478,336 B1 * | 10/2022 | Shao .................... A61C 9/0046 |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2012/0015316 A1 | 1/2012 | Sachdeva et al. |
| 2013/0204599 A1 | 8/2013 | Matov et al. |
| 2016/0135925 A1 | 5/2016 | Mason et al. |
| 2016/0242870 A1 | 8/2016 | Matov et al. |
| 2016/0310235 A1 | 10/2016 | Derakhshan et al. |
| 2017/0273760 A1 | 9/2017 | Morton et al. |
| 2018/0028294 A1 * | 2/2018 | Azernikov ........... G06K 9/6274 |
| 2018/0168775 A1 | 6/2018 | Derakhshan et al. |
| 2018/0280118 A1 | 10/2018 | Cramer |
| 2019/0029784 A1 | 1/2019 | Moalem et al. |
| 2019/0053876 A1 | 2/2019 | Sterental et al. |
| 2019/0076214 A1 | 3/2019 | Nyukhtikov et al. |
| 2019/0175303 A1 | 6/2019 | Akopov et al. |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2020/0000552 A1 | 1/2020 | Mednikov et al. |

(56) References Cited

U.S. PATENT DOCUMENTS

| | | |
|---|---|---|
| 2020/0000554 A1 | 1/2020 | Makarenkova et al. |
| 2020/0000555 A1 | 1/2020 | Yuryev et al. |
| 2020/0085546 A1 | 3/2020 | Li et al. |
| 2020/0105028 A1 | 4/2020 | Gao et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0315744 A1 | 10/2020 | Cramer |
| 2020/0360109 A1 | 11/2020 | Gao et al. |
| 2021/0134436 A1 | 5/2021 | Meyer et al. |
| 2021/0174477 A1 | 6/2021 | Shi et al. |

\* cited by examiner

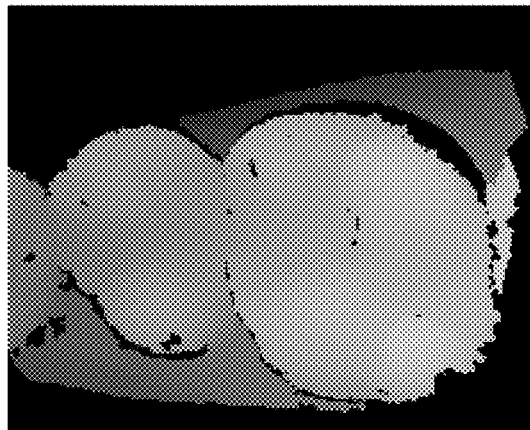 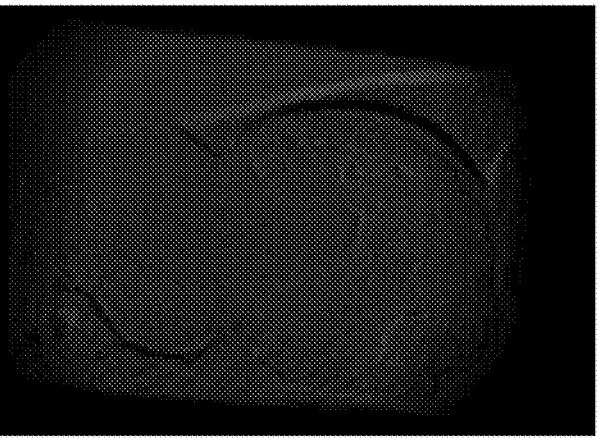
FIG. 5A  FIG. 5B
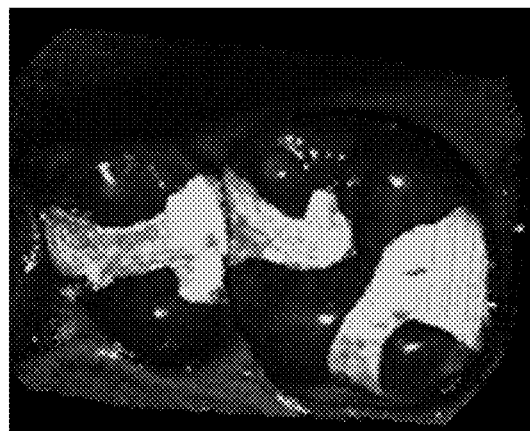 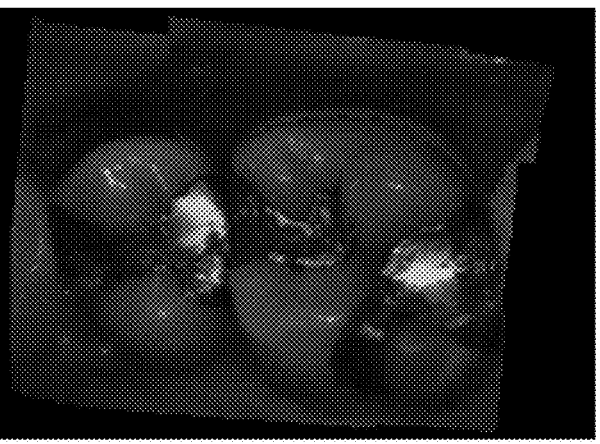
FIG. 5C  FIG. 5D
FIG. 5E  FIG. 5F

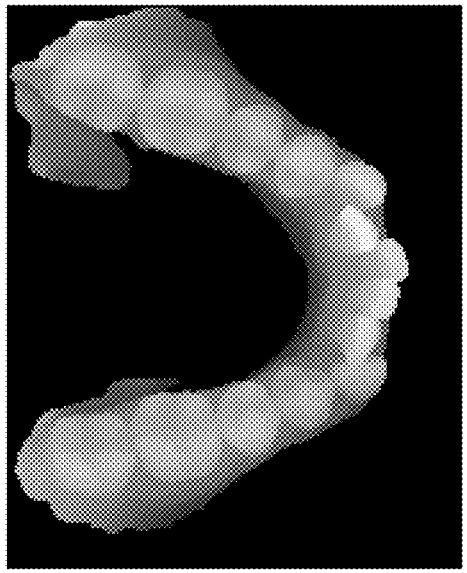 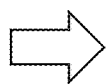 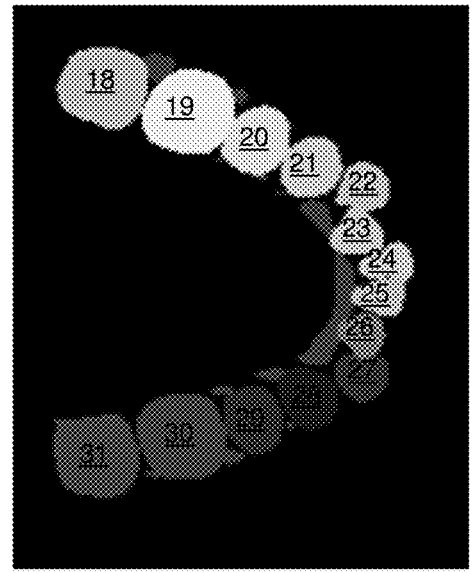

FIG. 8A     FIG. 8B

Given a height map, first separate each tooth as a separate instance. At the same time calculate tooth numbering probabilities for each instance
901

Assign jaw ordering to all tooth instances (using, e.g., Held-Karp algorithm for traveling salesman problem).
903

Obtain the maximum likelihood estimate of all tooth probabilities jointly across the jaw, preserving dental ordering (molar -> premolar -> canine, etc.).
905

FIG. 9

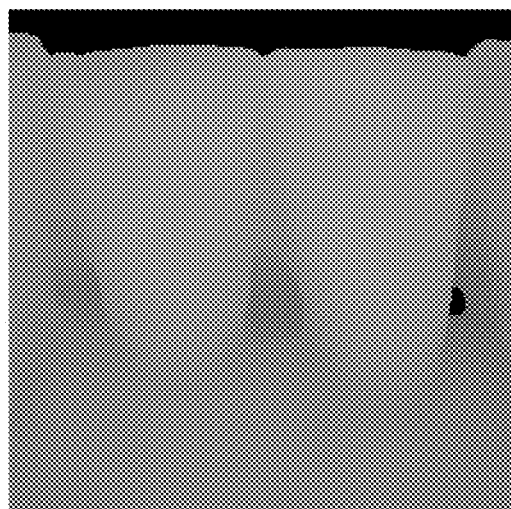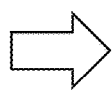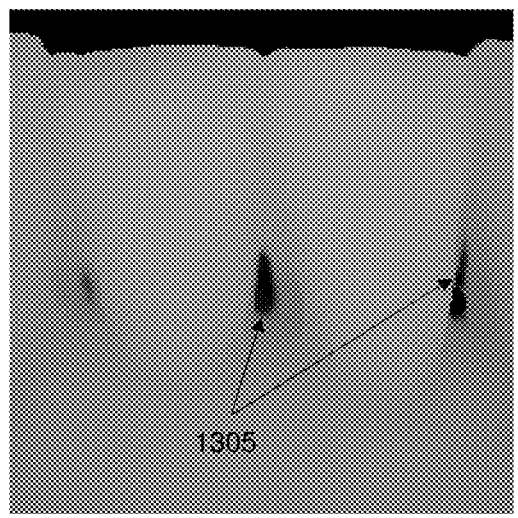
FIG. 13A                    FIG. 13B
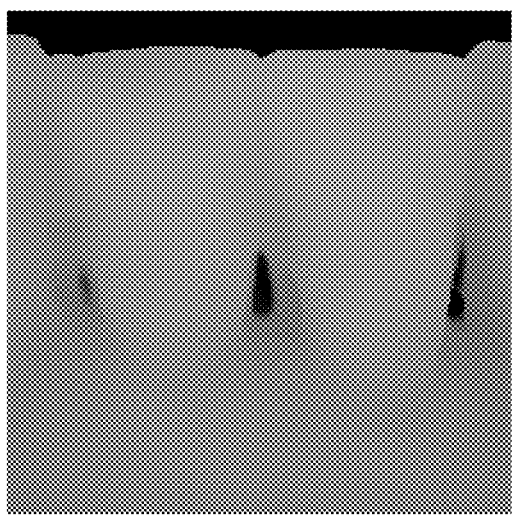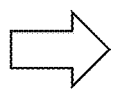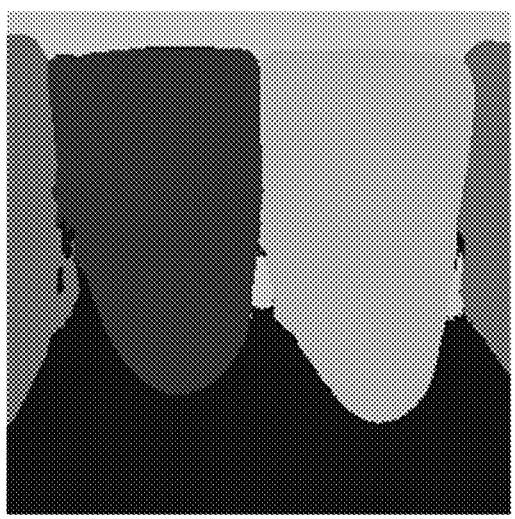
FIG. 14A                    FIG. 14B Accessing (e.g., receiving, gathering, taking, collecting, etc.) a first set of two-dimensional (2D) images of a subject's oral cavity. The 2D images may each have areas that can be segmented into a plurality of dental classes and may each relate (e.g., have a first relationship, such as 2D-3D projection values) to a first three-dimensional (3D) model of the subject's oral cavity, and may each include height map data representing distances between the subject's oral cavity and an image capture device
2001

Accessing (e.g., using) one or more automated machine learning agents that are trained to modify one or more second 3D models into the plurality of dental classes, the trained modifications using second height map data of a plurality of second 2D images and further using second relationships between the plurality of second 2D images and the one or more second 3D models
2003

Instructing the one or more automated machine learning agents to use the first height map data to modify the first areas of the first set of 2D images to get a plurality of modified first 2D images (e.g., a second set of 2D images, modified from the first set by the automated machine learning agents)
2005

Using the first relationships and the plurality of modified first 2D images to modify first mesh regions of the first 3D model (e.g., corresponding to the first areas of the plurality of first 2D images)
2007

FIG. 20

APPARATUSES AND METHODS FOR THREE-DIMENSIONAL DENTAL SEGMENTATION USING DENTAL IMAGE DATA

PRIORITY CLAIM

This application claims priority to U.S. Provisional Patent Application No. 62/896,509, filed Sep. 5, 2019, titled "APPARATUSES AND METHODS FOR THREE-DIMENSIONAL DENTAL SEGMENTATION," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein relate to computer-assisted dentistry and orthodontics, and more particularly to processing of three-dimensional (3D) dental models using data from dental scans and/or dental images.

BACKGROUND

Tools for two-dimensional (2D) and three-dimensional (3D) digital image technology are becoming increasingly useful in assisting in dental and orthodontic treatment. Treatment providers may use some form of digital image technology to study the dentitions of subjects. 2D and 3D image data may be used to form a digital model of a subject's dentition, including models of individual dentition components. Such models are useful, among other things, in developing an orthodontic treatment plan for the subject, as well as in creating one or more orthodontic appliances to implement the treatment plan. While it would be desirable to accurately segment, modify, update, and/or process 3D dental models, existing techniques make it difficult to do so.

SUMMARY OF THE DISCLOSURE

Described herein are systems and methods for generating high accurate and segmented models of a subject's oral cavity. These models may be easily manipulated by a dental practitioner, e.g., use such as a doctor, orthodontist, dental professional, etc. These methods and apparatuses may include image generation, generative Adversarial Networks, and the like.

For example, described herein are computer-implemented methods. These methods may be configured to segment a 3D model by processing a plurality of carefully selected 2D images, including segmenting these 2D images, combining the segmentation data, and applying the 2D segmentation data to a 3D model. For example a method may include: identifying a plurality of two-dimensional (2D) images of a subject's oral cavity, wherein the 2D images correspond to a digital three-dimensional (3D) model of the subject's oral cavity; processing the plurality of 2D images to segment each 2D image into a plurality of different structures; and projecting the segmented 2D images onto the 3D model to form a segmented 3D model.

The method may also include collecting the plurality of 2D images. For example, collecting the plurality of 2D images by identifying a view of the 3D model and generating a 2D projection of the 3D model from the view, and/or collecting the plurality of 2D images from scanned images of the subject's oral cavity.

Any of these methods may also or alternatively include modifying the 2D images; for example, adjusting a height map of each 2D image. Processing the plurality of 2D images may include applying a trained machine-learning agent to segment each of the 2D images. For example, processing may comprise using a conditional Generative Adversarial Network.

In any of these methods, projecting the segmented 2D images onto the 3D model may include resolving conflicts between the segmentation of each 2D image where a plurality of 2D images project to the same location on the 3D model. For example, resolving the conflicts may comprise applying Bayes' Theorem or voting on a per-location basis in the 3D model based on the plurality of 2D images that project onto the location.

A computer-implemented method may include: generating a plurality of interproximal separation planes between teeth of a digital three-dimensional (3D) model of a subject's oral cavity; collecting a two-dimensional (2D) images corresponding to each of one or more of: buccal, lingual and occlusal views, wherein the 2D images correspond to projections of the 3D model that are taken perpendicular to an interproximal separation plane of the plurality of interproximal separation planes; segmenting the 2D images to identify the boundaries between different components within the 2D images, wherein the components comprise teeth; combining the segmented 2D images to form a consensus segmentation of locations on the 3D model; and applying the consensus segmentation to the 3D model to form a segmented 3D model of the subject's oral cavity.

Any of these methods may include numbering the teeth of the 2D images using the 3D model or numbering the teeth in the 2D images and applying the numbering to the 3D model.

Any of these methods may include enhancing the 2D images prior to segmenting the 2D images in order to generate an enhanced 3D model. For example, enhancing may include adjusting the interproximal region between two or more teeth in the 2D images. Segmenting may include applying a trained machine-learning agent to segment each of the 2D images. In some variations, segmenting comprises using a conditional Generative Adversarial Network. Any of these methods may include segmenting the gingiva by identifying the segmented teeth in the segmented 3D model.

As mentioned, combining the segmented 2D images may include applying Bayes' Theorem or voting for specific locations on the 3D model that are represented by a plurality of 2D images.

In general, any the methods described herein may be performed by a system including one or more processors and a memory including instructions to perform the method. For example, as described herein, a system may include: one or more processors; a memory coupled to the one or more processors, the memory configured to store computer-program instructions, that, when executed by the one or more processors, perform a computer-implemented method comprising: identifying a plurality of two-dimensional (2D) images of a subject's oral cavity, wherein the 2D images correspond to a digital three-dimensional (3D) model of the subject's oral cavity; processing the plurality of 2D images to segment each 2D image into a plurality of different structures; and projecting the segmented 2D images onto the 3D model to form a segmented 3D model. The system may be configured to perform any of the steps described herein. These systems may include any of the modules or engines discussed herein.

For example, a system may include: one or more processors; a memory coupled to the one or more processors, the memory configured to store computer-program instructions, that, when executed by the one or more processors, perform a computer-implemented method comprising: generating a plurality of interproximal separation planes between teeth of a digital three-dimensional (3D) model of a subject's oral cavity; collecting a two-dimensional (2D) images corresponding to each of one or more of: buccal, lingual and occlusal views, wherein the 2D images correspond to projections of the 3D model that are taken perpendicular to an interproximal separation plane of the plurality of interproximal separation planes; segmenting the 2D images to identify the boundaries between different components within the 2D images, wherein the components comprise teeth; combining the segmented 2D images to form a consensus segmentation; and applying the consensus segmentation to the 3D model to form a segmented 3D model of the subject's oral cavity.

For example, described herein are computer-implemented methods, any of which may include: identifying a plurality of two-dimensional (2D) images of a subject's oral cavity, wherein the 2D images correspond to a digital three-dimensional (3D) model of the subject's oral cavity; processing the plurality of 2D images to segment each 2D image into a plurality of different structures; and projecting the segmented 2D images onto the 3D model to form a segmented 3D model.

The methods and apparatuses described herein may also include collecting the plurality of 2D images. For example, any of these methods or apparatuses may include collecting the plurality of 2D images by identifying a view of the 3D model and generating a 2D projection of the 3D model from the view. In some variations, the method, or an apparatus configured to perform the method, may include collecting the plurality of 2D images from scanned images of the subject's oral cavity.

In particular, any of these methods and apparatuses described herein may be configured to include modifying the 2D images. For example, modifying may include adjusting a height map of each 2D image.

In general, processing the plurality of 2D images may include applying a trained machine-learning agent to segment each of the 2D images. For example, processing may include using a conditional Generative Adversarial Network.

Any of these methods (or an apparatus configured to perform them) may include projecting the segmented 2D images onto the 3D model which comprises resolving conflicts between the segmentation of each 2D image based on the projection onto the 3D model.

In general, resolving the conflicts comprises applying Bayes' Theorem or voting. For example, combining the segmented 2D images may comprise applying Bayes' Theorem for a plurality of 2D images which represent overlapping locations on the 3D model in order to create a probability distribution of dental types per location in the 3D model. Any of these methods may include numbering the teeth of the 2D images using the 3D model or numbering the teeth in the 2D images in order to find the tooth numbers of locations on the 3D model.

For example, segmenting comprises applying a trained machine-learning agent to segment each of the 2D images into their relevant dental types. Segmenting may include using a conditional Generative Adversarial Network. Segmenting may include segmenting the gingiva by identifying the segmented teeth and gingiva in the segmented 3D model.

A computer-implemented method may include: generating a plurality of interproximal separation planes between teeth of a digital three-dimensional (3D) model of a subject's oral cavity; collecting a two-dimensional (2D) images corresponding to each of one or more of: buccal, lingual and occlusal views, wherein the 2D images correspond to projections of the 3D model that are taken perpendicular to an interproximal separation plane of the plurality of interproximal separation planes; segmenting the 2D images to identify the boundaries between different components within the 2D images, wherein the components comprise teeth; combining the segmented 2D images to form a consensus segmentation; and applying the consensus segmentation to the 3D model to form a segmented 3D model of the subject's oral cavity.

As mentioned, also described herein are systems, including systems configured to perform any of the methods described herein. For example, a system may include: one or more processors; a memory coupled to the one or more processors, the memory configured to store computer-program instructions, that, when executed by the one or more processors, perform a computer-implemented method comprising: identifying a plurality of two-dimensional (2D) images of a subject's oral cavity, wherein the 2D images correspond to a digital three-dimensional (3D) model of the subject's oral cavity; processing the plurality of 2D images to segment each 2D image into a plurality of different structures; and projecting the segmented 2D images onto the 3D model to form a segmented 3D model.

A system may include: one or more processors; a memory coupled to the one or more processors, the memory configured to store computer-program instructions, that, when executed by the one or more processors, perform a computer-implemented method comprising: generating a plurality of interproximal separation planes between teeth of a digital three-dimensional (3D) model of a subject's oral cavity; collecting a two-dimensional (2D) images corresponding to each of one or more of: buccal, lingual and occlusal views, wherein the 2D images correspond to projections of the 3D model that are taken perpendicular to an interproximal separation plane of the plurality of interproximal separation planes; segmenting the 2D images to identify the boundaries between different components within the 2D images, wherein the components comprise teeth; combining the segmented 2D images to form a consensus segmentation; and applying the consensus segmentation to the 3D model to form a segmented 3D model of the subject's oral cavity.

The computer-implemented method incorporated as part of the system may include any of the steps and variations of steps described above and herein.

Also described herein are methods, including methods of segmenting a 3D model, that include: accessing a plurality of first two-dimensional (2D) images, wherein the plurality of first 2D images: represents a subject's oral cavity, each has first areas that can be segmented into a plurality of dental classes, each has a first relationship to a first three-dimensional (3D) model of the subject's oral cavity, and each has first height map data representing distances between the subject's oral cavity and an image capture device; accessing one or more automated machine learning agents trained to modify one or more second 3D models into the plurality of dental classes, the trained modifications using second height map data of a plurality of second 2D images and further using second relationships between the plurality of second 2D images and the one or more second 3D models; instructing the one or more automated machine learning agents to use the first height map data to modify the first areas of the plurality of first 2D images to get a plurality of modified first 2D images; and using the first relationships and the plurality of modified first 2D images to modify first mesh regions of the first 3D model corresponding to the first areas of the plurality of first 2D images.

Any of these methods may also include: gathering the plurality of second 2D images from a training datastore; identifying one or more modifications to second areas of the plurality of second 2D images; training the one or more automated machine learning to use the second height map data to provide the one or more modifications to the second areas of the plurality of second 2D images to get a plurality of modified second 2D images; and training the one or more automated machine learning to use the second relationships and the plurality of modified second 2D images to modify second mesh regions of the one or more second 3D models corresponding to the second areas.

In general, accessing the plurality of first 2D images may include gathering the plurality of first 2D images. The first relationship may be represented by 2D-3D projection values to project portions of the plurality of first 2D images onto the first 3D model.

In any of these methods, the one or more automated machine learning agents may include a classifier trained to modify the one or more second 3D models. For example, the one or more automated machine learning agents may comprise a Generative Adversarial Network (GAN) trained to modify the one or more second 3D models. In some variations, the one or more automated machine learning agents comprises a conditional Generative Adversarial Network (cGAN) trained to segment the one or more second 3D models into the plurality of dental classes.

The first 3D model may include a 3D mesh of the subject's oral cavity, the one or more second 3D models comprise one or more 3D meshes of a plurality of oral cavities, or some combination thereof.

In any of these methods, the step of using the first relationships and the modified first 2D images to modify the first 3D model may include mapping one or more pixel values from pixels of the plurality of modified first 2D images onto one or more faces of a mesh of the first 3D model. For example, using the first relationships and the modified first 2D images to modify the first 3D model may include representing the plurality of dental classes using a plurality of color channels.

The methods described herein may include instructing the one or more automated machine learning agents to use a plurality of data types from the plurality of first 2D images modify the first areas of the plurality of first 2D images to get the plurality of modified first 2D images. For example, these methods may include instructing the one or more automated machine learning agents to use color data, count map data, texture data, grading data, or some combination thereof, from the plurality of first 2D images modify the first areas of the plurality of first 2D images to get the plurality of modified first 2D images.

In any of these methods, using the first relationships and the plurality of modified first 2D images to modify the first mesh regions may include segmenting the first 3D model using the modified first 2D images and the first relationships. For example, the trained modifications may comprise one or more segmentations segmenting the second 3D models into a plurality of dental classes. In some variations the trained modifications comprise one or more segmentations segmenting the second 3D models into a plurality of dental classes. At least some of the plurality of dental classes may comprise teeth, gums, and excess materials, or some combination thereof. In some variations the trained modifications may include one or more segmentations segmenting the second 3D models into a plurality of dental classes. At least some of the plurality of dental classes may comprise a plurality of anatomical tooth identifiers.

In any of these methods, the trained modifications may include one or more segmentations segmenting the second 3D models into a plurality of dental classes, and at least some of the plurality of dental classes may comprise extra-oral objects, dental appliances, oral soft tissue, or some combination thereof. For example, the trained modifications may include one or more segmentations segmenting the second 3D models into a plurality of dental classes, and the plurality of dental classes may comprise binary values, discrete values, or some combination thereof representing existence or non-existence of one or more portions of dental anatomy. In some variations the trained modifications comprise one or more segmentations segmenting the second 3D models into a plurality of dental classes, and the plurality of dental classes may comprise continuous values related a target height map for the first 3D model. The trained modifications may comprise one or more segmentations segmenting the second 3D models into a plurality of dental classes, and the first relationships may represent projections of pixels on the each of the plurality of first 2D images to one or more faces of a mesh of the first 3D model.

The first relationships and the plurality of modified first 2D images to modify the first mesh regions may include improving representations of one or more features of the first 3D model using the modified first 2D images and the first relationships.

Any of these methods may also include: gathering the first 3D model and/or generating the first plurality of 2D images using one or more 3D-2D projection values to transfer portions of the first 3D model onto portions of the plurality of first 2D images.

The first areas of the plurality of first 2D images may comprise regions of limited or missing height map data. In some variations, instructing the one or more automated machine learning agents to use the first height map data to modify the first areas of the plurality of first 2D images may include adding new height map data to the first areas. For example, the plurality of first 2D images may comprise a plurality of 2D perspectives of the subject's oral cavity; in some variations the first areas of the plurality of first 2D images comprises an oral component to be modified. The method may further include instructing the one or more automated machine learning agents to use the first height map data to modify the first areas of the plurality of first 2D images comprises resolving one or more conflicts between conflicting representations of the oral component.

The plurality of first 2D images may comprise a plurality of 2D perspectives of the subject's oral cavity. The first areas of the plurality of first 2D images may include an oral component to be modified. Instructing the one or more automated machine learning agents to use the first height map data to modify the first areas of the plurality of first 2D images may include resolving one or more conflicts between conflicting representations of the oral component by using a statistical process to reconcile the one or more conflicts. For example, the first areas of the plurality of first 2D images may comprise interproximal regions of teeth within the subject's oral cavity, and instructing the one or more automated machine learning agents to use the first height map data to modify the first areas of the plurality of first 2D images may include updating representations of the interproximal regions. The plurality of first 2D images may comprise buccal views of the subject oral cavity, lingual views of the subject oral cavity, occlusal views of the subject oral cavity, or some combination thereof.

In some variations, the first relationships may provide mesial-distal projections of the first 3D model onto the plurality of first 2D images. For example, the first relationship may be represented by: 3D-2D projection values to transfer portions of the first 3D model onto the plurality of first 2D images, Delaunay triangulation, marching cubes, or some combination thereof.

Also described herein are systems including: one or more processors; memory storing computer-program instructions that, when executed by the one or more processors cause the system to implement a method comprising: accessing a plurality of first two-dimensional (2D) images, wherein the plurality of first 2D images: represents a subject's oral cavity, each has first areas that can be segmented into a plurality of dental classes, each has a first relationship to a first three-dimensional (3D) model of the subject's oral cavity, and each has first height map data representing distances between the subject's oral cavity and an image capture device; accessing one or more automated machine learning agents trained to modify to one or more second 3D models into the plurality of dental classes, the trained modifications using second height map data of a plurality of second 2D images and further using second relationships between the plurality of second 2D images and the one or more second 3D models; instructing the one or more automated machine learning agents to use the first height map data to modify the first areas of the plurality of first 2D images to get a plurality of modified first 2D images; and using the first relationships between the plurality of first 2D images and the first 3D models, and using the plurality of modified first 2D images to modify first mesh regions of the first 3D model corresponding to the first areas of the plurality of first 2D images.

Also described herein are methods including: gathering a plurality of first two-dimensional (2D) images, wherein the plurality of first 2D images: represents a subject's oral cavity, each has first areas that can be segmented into a plurality of dental classes, each has first projection values in relation to a first three-dimensional (3D) model of the subject's oral cavity, and each has first height map data representing distances between the subject's oral cavity and an image capture device; accessing one or more automated machine learning agents trained to segment one or more second 3D models into the plurality of dental classes, the trained segmenting using second height map data of a plurality of second 2D images and further using second projection values relating the plurality of second 2D images to the one or more second 3D models; instructing the one or more automated machine learning agents to use the first height map data to segment the first areas of the plurality of first 2D images into the plurality of dental classes to get a plurality of segmented first 2D images; and using the first projection values and the plurality of segmented first 2D images to segment the first 3D model of the subject's oral cavity into the plurality of dental classes.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 3A illustrates mapping of height map inputs to manually identified segmented images (FIG. 3B), and using this information to predict labels from 2D height maps (FIG. 3C).

in FIG. 4B just the segmented teeth are shown.

FIGS. 5A-5F illustrate information from 2D images that may be processed by the methods and systems described herein, and used to segment and/or modify the 3D models as described herein. FIG. 5A illustrates height map information, FIG. 5B illustrates a count map, FIG. 5C is a grades map, FIG. 5D illustrates texture, FIG. 5E shows labeled regions (e.g., empty space of tooth space), and FIG. 5F shows a prediction of labeled regions based on a machine learning agent as described below.

FIGS. 8A-8B schematically illustrate a putative numbering based on a height map.

FIG. 8A shows an unmodified buccal view of a subject's lower arch. FIG. 8B shows an example of a labeled set of teeth from FIG. 8A. In this example individual teeth are marked by both color and by number (e.g., alphanumeric label).

FIG. 9 schematically illustrates one example of tooth numbering based on height map information for one, or more preferably more, 2D images.

FIGS. 13A-13B illustrates a step of enhancing the identified projections and/or captured 2D images as described herein. FIG. 13A (similar to FIG. 12A) shows a buccal projection of the 3D model and FIG. 13B shows an enhanced version of the projection.

FIGS. 14A-14B illustrates further processing of 2D images, showing the use of the enhanced 2D images to determine segmentation.

FIG. 17A shows the mapping of the segmented 2D images to corresponding mesh points in the original scanned model. FIG. 17B shows the original model with the identified (e.g., segmented) teeth removed, after a hole-filling technique has been used on the remaining, gingival, tissue.

FIG. 20 illustrates one method of segmenting a 3D model as described herein.

DETAILED DESCRIPTION

Figure 1A:
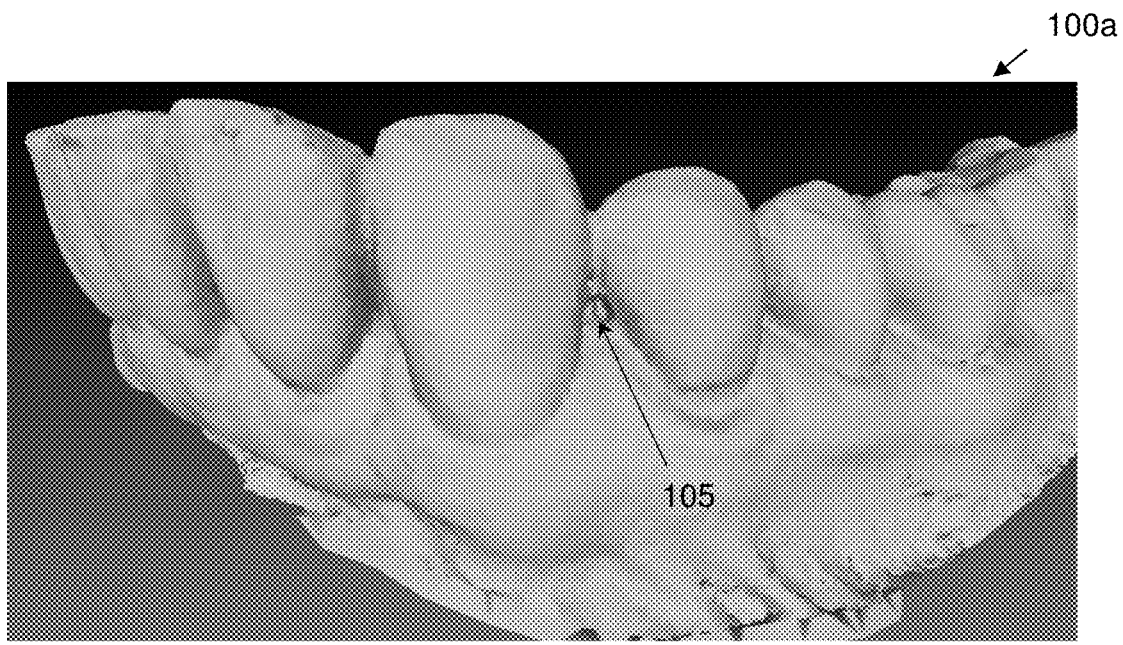
FIGS. 1A-1D illustrate examples of intraoral scans having regions that may be difficult to resolve using traditional segmentation techniques.
Figure 1B:
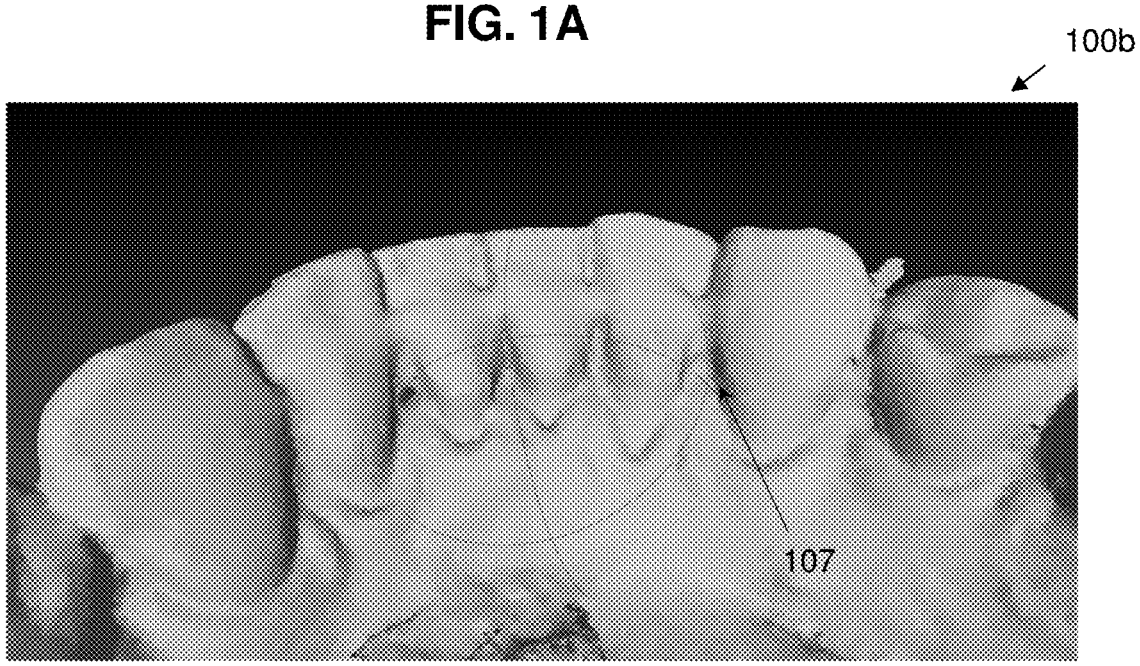
Figure 1C:
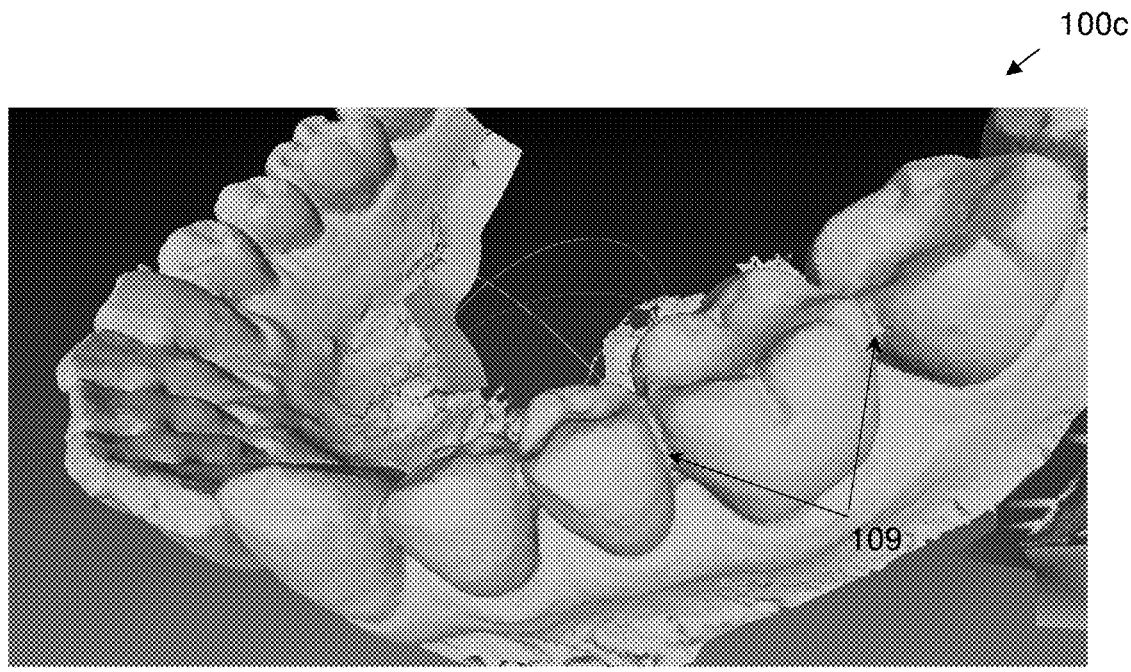
Figure 1D:
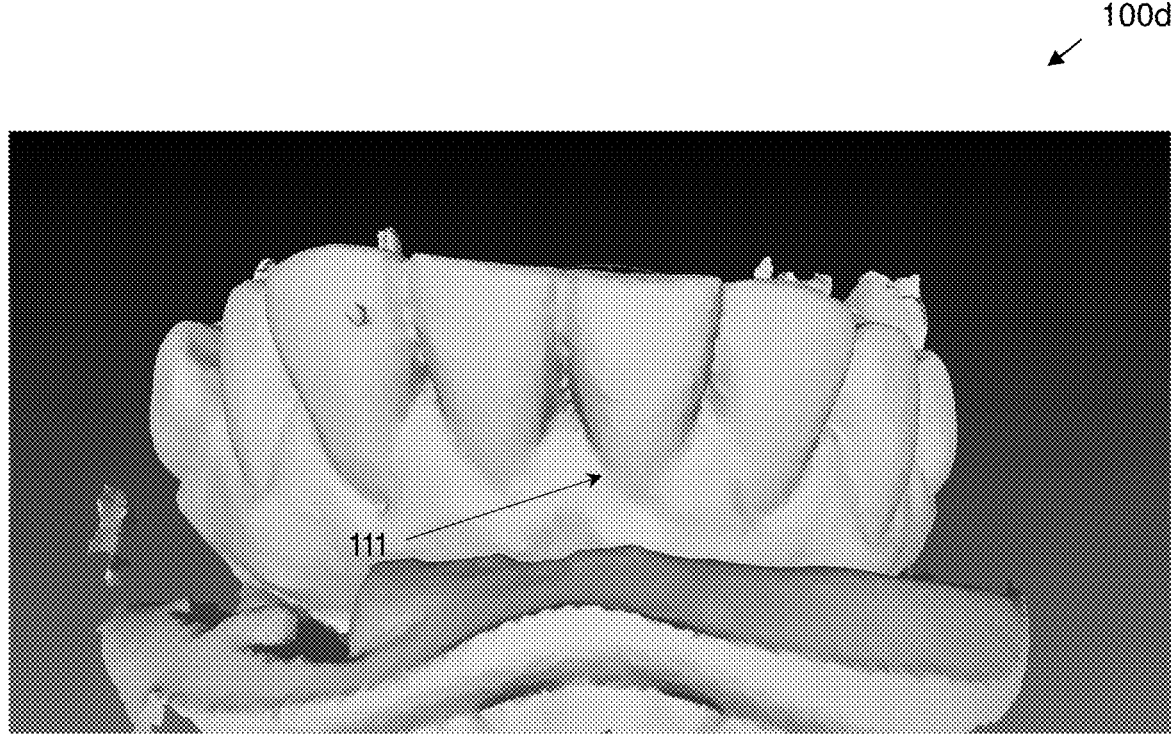

While desirable, accurately segmenting and representing the portions of a three-dimensional (3D) model of an oral cavity has proven difficult. One issue is that 3D models based on two-dimensional (2D) images, including those with height map information, do not accurately represent a subject's oral cavity. Representations of interproximal regions, gingival lines, and other regions may be inaccurate due to operation of the hardware and/or software used to capture 2D images of dentition. FIGS. 1A-1D illustrate examples of 3D models 100a-100d having regions that may be difficult to resolve using traditional segmentation techniques. In FIG. 1A, for example, a 3D model 100a comprises a closed region 105 in an interproximal area between two teeth. In FIG. 1B, a 3D model 100b comprises a closed region 107 in an interproximal area between adjacent teeth. In the examples of FIGS. 1A and 1B, the adjacent teeth around the closed regions 105 and 107 appear unseparated, with inaccurately sized and shaped gaps between the teeth. The 3D model 100c of FIG. 1C comprises two unclear separation areas 109 between a premolar tooth and its neighboring teeth. The 3D model 100d of FIG. 1D comprises an unclear separation area 111 between teeth and a gingival line. The unclear separation areas 109 and 111 do not accurately represent a subject's oral anatomy. For instance, the unclear separation area 109 does not show gaps between the premolar and its neighbors. The unclear separation area 111 does not show the line between the subject's gingiva and teeth. It would be difficult to use the 3D dental models 100a-100d for treatment planning due to inaccurate anatomical representations and other issues. Existing solutions to segment the 3D dental models 100a-100d involve manually review/labeling or processing the 3D model. Existing solutions are often computationally intensive and/or yield inaccurate results. The techniques described herein address issues associated with existing 3D modeling of a subject's oral cavity.

Figure 19:
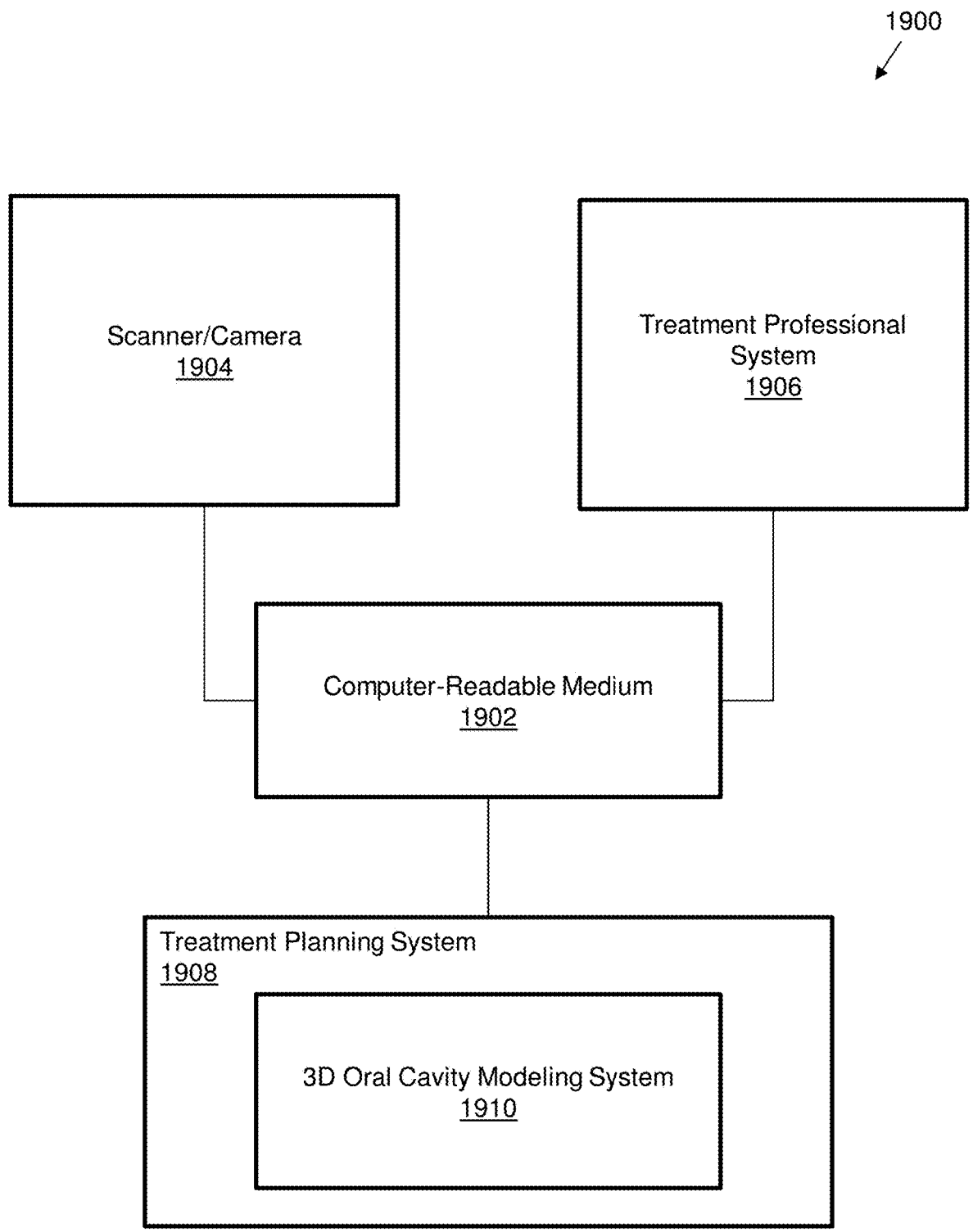
FIG. 19 shows a treatment planning ecosystem, in accordance with some implementations.

FIG. 19 shows a treatment planning ecosystem 1900, in accordance with some implementations. The treatment planning ecosystem 1900 includes a computer-readable medium 1902, a scanner/camera 1904, a treatment professional system 1906, and a treatment planning system 1908. The scanner/camera 1904, the treatment professional system 1906, and the treatment planning system 1908 may be coupled to one another over the computer-readable medium 1902. The computer-readable medium 1902 represents any transitory or non-transitory computer-readable medium or architecture capable of facilitating communication or data transfer. In one example, the computer-readable medium 1902 may facilitate communication between scanner/camera 1904, the treatment professional system 1906, and the treatment planning system 1910. In some implementations, computer-readable medium 1902 comprises a computer network that facilitates communication or data transfer using wireless and/or wired connections. Examples of computer-readable medium 1902 include, without limitation, an intranet, a Wide Area Network (WAN), a Local Area Network (LAN), a Personal Area Network (PAN), the Internet, Power Line Communications (PLC), a cellular network (e.g., a Global System for Mobile Communications (GSM) network), portions of one or more of the same, variations or combinations of one or more of the same, and/or any other suitable network. Computer-readable medium 1902 may also comprise a connection between elements inside a single computing device (e.g., the scanner/camera 1904, the treatment professional system 1906, the treatment planning system 1908, etc.). It is noted that while FIG. 19 shows the elements as distinct blocks, in various implementations, two or more of these blocks can be on the same computing device.

The scanner/camera 1904 may include a digital device operative to capture images. The scanner/camera 1904 may comprise an intraoral scanner, a camera, a desktop/laptop computer system, a mobile phone, a kiosk, or some combination thereof. In some implementations, the scanner/camera 1904 captures 2D images of an area of interest along with height map data, e.g., data representing a distance between a part of the scanner/camera 1904 and an object within the area of interest. In the dental context, the scanner/camera 1904 may capture a series of images of an oral cavity. Each image may have associated with it height map data that represents the distance between parts of the oral cavity and the scanner/camera 1904. Height map data may be represented in any format. In some implementations, height map data may be represented as colors, intensities, brightness, or other attributes of pixels on a 2D image. The scanner/camera 1904 may also capture projection values for each 2D image. The projection values may be associated with rotations and/or translations in space that represent how a 2D image is stitched into a 3D representation of the area of interest. As noted herein, projection values may represent how pixels on 2D images are projected to a face of a mesh on a 3D model of the area of interest. A "3D model" of a subject's dentition, as used herein, may include a three-dimensional representation of one or more surfaces corresponding to physical contours of the subject's dentition. A 3D model may include a set of shapes (e.g., triangles), that when combined together, form a "mesh" or contours of the 3D model. Each shape may comprise a "face" of the 3D model.

In some implementations, the scanner/camera 1904 captures data about color inputs and/or data that represents the texture of surfaces within an area of interest. The scanner/camera 1904 may record scan quality, e.g., data representing whether 2D images accurately represent an area of interest and/or whether there are flaws, such as holes or unclear areas, within 2D images of an area of interest. In some implementations, the scanner/camera 1904 captures data related to numbers of raw scans contributing to scan pixels within 2D images.

The treatment professional system 1906 may include a computing device capable of reading computer-executable instructions. The treatment professional system 1906 may be, for example, a desktop computer, a tablet computing device, a laptop, a smartphone, an augmented reality device, or other consumer device. Additional examples of the treatment professional system 1906 include, without limitation, laptops, tablets, desktops, servers, cellular phones, Personal Digital Assistants (PDAs), multimedia players, embedded systems, wearable devices (e.g., smart watches, smart glasses, etc.), smart vehicles, smart packaging (e.g., active or intelligent packaging), gaming consoles, Internet-of-Things devices (e.g., smart appliances, etc.), variations or combinations of one or more of the same, and/or any other suitable computing device.

In various implementations, the treatment professional system 1906 is configured to interface with a dental professional. A "dental professional" (used interchangeably with dentist, orthodontist, and doctor herein) as used herein, may include any person with specialized training in the field of dentistry, and may include, without limitation, general practice dentists, orthodontists, dental technicians, dental hygienists, etc. A dental professional may include a person who can assess, diagnose, and/or treat a dental condition. "Assessment" of a dental condition, as used herein, may include an estimation of the existence of a dental condition. An assessment of a dental condition need not be a clinical diagnosis of the dental condition. In some embodiments, an "assessment" of a dental condition may include an "image based assessment," that is an assessment of a dental condition based in part or on whole on photos and/or images (e.g., images that are not used to stitch a mesh or form the basis of a clinical scan) taken of the dental condition. A "diagnosis" of a dental condition, as used herein, may include a clinical identification of the nature of an illness or other problem by examination of the symptoms. "Treatment" of a dental condition, as used herein, may include prescription and/or administration of care to address the dental conditions. Examples of treatments to dental conditions include prescription and/or administration of brackets/wires, clear aligners, and/or other appliances to address orthodontic conditions, prescription and/or administration of restorative elements to address bring dentition to functional and/or aesthetic requirements, etc.

The treatment planning system 1908 may include a computing device capable of reading computer-executable instructions. The treatment planning system 1908 may provide to a user (e.g., a user of the treatment professional system 1906) software (e.g., one or more webpages, stand-alone applications (e.g., dedicated treatment planning and/or treatment visualization applications), mobile applications, etc.) that allows the user to interact with subjects (e.g., those people whose intraoral cavities are being imaged by the scanner/camera 1904), create/modify/manage treatment plans. The treatment planning system 1908 may be configured to process 2D images captured at the scanner/camera 1904, generate 3D dental models using the 2D images, and/or generate treatment plans for subjects whose dentition has been scanned/imaged. In some implementations, the treatment planning system 1908 identifies an initial position of a subject's dentition, an intended final position of the subject's dentition, and/or a plurality of intermediate positions to move the subject's dentition toward the intended final positions. In some implementations, the treatment planning system 1908 operates with user input, e.g., with a technician and/or dental professional managing a treatment plan. In various implementations, however, some or all of the modules of the treatment planning system 1908 can operate using automated agents and without human intervention.

In the example of FIG. 19, the treatment planning system 1910 includes a 3D oral cavity modeling system 1910. The 3D oral cavity modeling system 1910 may execute one or more automated agents that operate to process 3D dental models of a subject's oral cavity using data from dental scans and/or dental images. Examples of data from dental scans/images that can be used for this purpose include height map data, data about color inputs and/or textures, data about scan/image qualities, data about how many counts of raw scans are in height map pixels, etc. The 3D oral cavity modeling system 1910 may use data from dental scans and/or dental images to predict dental classes used to segment a 3D model of a subject's dentition. The 3D oral cavity modeling system 1910 may process the 2D images using manual, semi-manual, or automatic processing techniques. As will be described in greater detail herein, in some variations the processing may be driven, performed and/or guided by a machine learning agent. The machine learning agent may be trained on a variety of different datasets and may be adaptively trained, so that it may update/modify its behavior over time. Any machine learning agent herein may use a "classifier," which as used herein, may include one or more automated agents operative to learn how to assign classes to one or more items and assign those classes to those items. A classifier may be trained by training data, which as used herein, may include any data to set initial observations from a classifier may learn and/or adapt.

"Segmenting" a representation of a subject's dentition, such as a 2D image or a 3D model of a subject's dentition, as used herein, may include labeling dental classes in the representation. Non-exclusive examples of dental classes include items corresponding to a subject's oral anatomy (teeth, gums, lips, tongue, other oral soft tissue, etc.) and items not corresponding to a subject's oral anatomy (non-oral anatomical items (e.g., fingers), non-anatomical items (dental appliances, foreign objects, etc.). Additional non-exclusive examples of dental classes include: teeth and/or particular teeth (e.g., teeth identified by tooth shape and/or anatomical tooth number), gingiva, and other items (excess materials, e.g., the subject's palate, the subject's tongue, other oral soft tissue of the subject, a finger or other non-oral part of the subject's body, a dental appliance on the patient's teeth, etc.). Segmentation may involve assigning each point in a 3D model of a subject's dentition an appropriate dental class. In some implementations, segmenting a 3D model of a subject's dentition may involve determining whether the various region of the 3D model correspond to specific teeth, gums, or excess materials, and labeling those regions appropriately.

The 3D oral cavity modeling system 1910 may further use data from dental scans and/or dental images to modify and/or update 3D models of a subject's dentition so they are more accurate and relevant to treatment planning. As examples, the 3D oral cavity modeling system 1910 may modify interproximal regions, gingival boundaries, and/or other areas of a 3D model to make these regions more accurate and/or truer depictions to a subject's intraoral cavity.

In some embodiments, the 3D oral cavity modeling system 1910 executes automated agents that use artificial intelligence and/or machine learning to predict dental classes in 3D dental models using data from dental scans and/or dental images. In some implementations, the 3D oral cavity modeling system 1910 uses a neural network to classify data from dental scans and/or dental images into appropriate dental classes. As an example, the 3D oral cavity modeling system 1910 may map height map data and pixel data to a set of human-labeled segmented images. The 3D oral cavity modeling system 1910 may derive one or more processes that, when executed, predict dental class labels directly from height maps. In various implementations, labels can be binary and/or discrete (e.g. with values corresponding to different dental classes), continuous (e.g., values ranging through a target height map), etc. The 3D oral cavity modeling system 1910 may use a conditional Generative Adversarial Network (cGAN) and/or any other machine learning system to classify data from dental scans and/or dental images into dental classes. As noted herein, the 3D oral cavity modeling system 1910 may be trained with a library of labeled and/or accurately modeled 2D dental scans and/or dental images.

The 3D oral cavity modeling system 1910 may process 2D dental scans and/or 2D dental images in one or more ways, including segmenting the images, and/or enhancing the images, including the interproximal regions, the height maps, etc.

The 3D oral cavity modeling system 1910 may modify, e.g., segment, a 3D model of a subject's oral cavity with modules or engines that may perform operations using one or more processors for digitally processing the 3D model, and in particular for processing 2D images associated with the 3D model so that modifications made to the 2D images may be translated, including mapped, to the 3D model. The 3D oral cavity modeling system 1910 may be configured to receive data, such as subject scan data and/or 3D model data either directly (e.g., from the scanner/camera 1904), and/or indirectly, such as from a memory storing a digital model and/or 2D scan images from the subject's oral cavity (e.g., on the treatment planning system 1908). The 3D oral cavity modeling system 1910 may processes these images and/or 3D model(s) and may output, including displaying, storing and/or transmitting, the 3D model of the subject's oral cavity. In some variation the apparatus may be part of another apparatus (e.g., system) for treating a subject, including for generating a treatment plan and/or generating a series of dental appliances for performing the treatment plan.

The 3D oral cavity modeling system 1910 may generally improve the 2D images and/or the 3D models of the subject's oral cavity, which may be used in a variety of beneficial ways; in particular a segmented and/or corrected 3D model as described herein may be used to generate a treatment plan for modifying (e.g., correcting) a subject's dentition. In any of the methods and apparatuses described herein, the 3D model may be used to generate one or more (e.g., a series) of dental appliances, such as but not limited to orthodontic aligners for re-aligning teeth. As will be described in greater detail below, there are a number of indication, treatments, and processes that may benefit from the segmented and/or corrected 3D models and 2 images described herein. Thus any of the methods and apparatuses described herein may be part of a method or apparatus (e.g., system) for performing any of these treatments, processes, or the like.

The 3D oral cavity modeling system 1910 may execute automated agents that use projection values of 2D dental scans and/or dental images to project attributes of the scans/images onto a 3D model. As noted herein, pixel values within 2D dental scans and/or dental images may include height map information representing distances of objects from the scanner/camera 1904 or visible light information as observed at the location of the scanner/camera 1904. When projected to a 3D model of an object (e.g., a subject's dentition) within an area of interest, the height map information may represent depictions of corresponding faces of a mesh of the 3D model. Automated agents executed by the 3D oral cavity modeling system 1910 may further resolve one or more conflicts between providing segmentation results on 2D images. Conflicts can be resolved statistically and, e.g., can involve taking consensuses, determining probabilities that a specific segmentation result is valid, etc. As an example, the 3D oral cavity modeling system 1910 may execute agents that implement Bayesian rules to combine multiple segmentation results with each other.

The 3D oral cavity modeling engine 1910 may use processed 2D images to modify a 3D model, either by revising the 3D model (e.g., surfaces) based on the processed 2D images, and/or by mapping components in the processed 2D images to components in the 3D model. In some variations, the 3D model may be a mesh model of at least a portion of the subject's oral cavity, and may include mesh points. Individual or groups of mesh points may include data that indicates features (labels, such as tooth number, color, etc.) extracted from the 2D images, and/or from the processed 2D images.

The 3D oral cavity modeling system 1910 can accurately create and/or update a 3D dental model and the ability to predict multiple dental classes concurrently. The 3D oral cavity modeling system 1910 can also accurately segment 3D models of an oral cavity and associated structures (e.g., teeth, gingiva and/or palatal region), where each point in the 3D model, e.g., in some variations in a mesh forming the 3D model, that are labeled according to an appropriate dental class.

FIG. 2 shows an example of a 3D oral cavity modeling system 250. The 3D oral cavity modeling system 250 may correspond to an example of the 3D oral cavity modeling system 1910, discussed further herein. It is noted that, as an example of the 3D oral cavity modeling system 1910, the 3D oral cavity modeling system 250 may include modules and/or implement functionalities different than the 3D oral cavity modeling system 1910 The 3D oral cavity modeling system 250 may include one or more engines and datastores. A computer system can be implemented as an engine, as part of an engine or through multiple engines. As used herein, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like.

As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end-users access through a web browser or container application without having the functionalities and/or modules installed locally on the end-users' computing devices.

As used herein, datastores are intended to include repositories having any applicable organization of data, including images, 3D models, tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in nontrivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

Figure 2A:
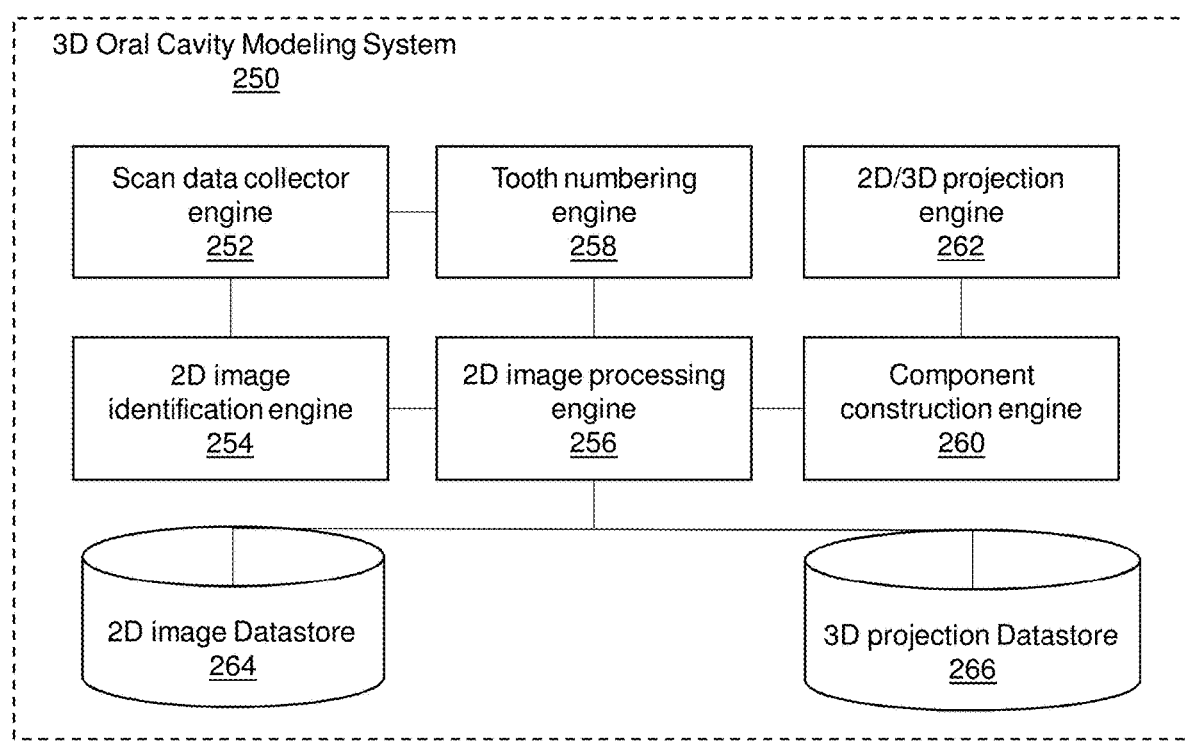
FIG. 2A shows one variation of a schematic illustration of a system for three-dimensional (3D) modeling of a subject's oral cavity.

The 3D oral cavity modeling system 250 may include a computer-readable medium and one or more processors (or may be configured for operating one or more processors). In FIG. 2A the schematic of the 3D oral cavity modeling system 250 includes a scan data collector engine 252, a tooth numbering engine 258, a 2D image identification engine 254, a 2D image processing engine 256, a component construction engine 260, a 2D/3D projection engine 262, a 2D image datastore and a 3D projection datastore 266. The various engines (e.g., modules) and datastores of the system may be coupled to one another (e.g., through the example couplings shown in FIG. 2A) or to components not explicitly shown in FIG. 2A. The computer-readable medium may include any computer-readable medium, including without limitation a bus, a wired network, a wireless network, or some combination thereof.

The engine(s) included in the systems, and in particular the 2D image processing engine 256, may implement one or more automated agents (e.g., artificial intelligence and/or machine learning agents) that process 2D images, as will be described in greater detail below. For example, in various implementations, a 2D image processing engine 256 may implement one or more automated agents configured to determine segmentation based on the 2D image or a collection of images. The automated agent may be trained using a prepared dataset, e.g., from within the 2D image datastore 264 that may be manually segmented. In some variations, an automated agent may identify interproximal spacing in the 2D images, and may be trained on a prepared dataset of 2D images.

The system shown in FIG. 2A may also include a tooth numbering engine 258 that may use one or more techniques (including machine learning techniques) to estimate an order of teeth based, e.g., on location and/or a height map from various 2D images. The 2D image processing engine 256 and/or the 2D image identification engine 254 may receive input from the tooth numbering engine 258. In some variations the identification of tooth numbering by the tooth numbering engine may be iterative, as the identified tooth numbering may be modified by the system.

As mentioned, the tooth numbering engine 258 may be automatically or semi-automatically determine or suggest the numbering of the teeth within the oral cavity. A tooth type identifier datastore may be configured to store one or more tooth type identifiers of different tooth types. In some implementations, the tooth type identifiers correspond to numbers of a Universal Tooth Numbering System, character strings to identify tooth types by anatomy, images or portions thereof to identify tooth types by geometry and/or other characteristics, etc. The tooth numbering engine 258 may implement one or more automated agents configured to gather tooth type identifiers. In some implementations, a tooth type identifier gathering engine may gather a series of tooth type identifiers corresponding to the teeth in a human being's permanent/adult dentition. The tooth type identifier gathering engine may gather from a tooth type identifier datastore including universal or other tooth numbering system, character identifiers, image(s), etc. corresponding to a person's adult teeth. In various implementations, the tooth type identifier gathering engine may provide tooth types to other modules, as mentioned above.

In FIG. 2A, the 2D image identification engine 254 may identify which 2D images, including in some variations which projections from the 3D model, may be processed to improve the 3D model, including for determining segmentation. These 2D images may be selected and/or generated and may be processed (e.g., using the 2D image processing engine) and may be stored in a processed 2D image database or Datastore (not shown in FIG. 2A).

The system of FIG. 2A may include a component construction engine that may apply the processed 2D images to the 3D model in order to refine the 3D model. In some variations the system may reconstruct the 3D model from the processed 2D images. In some variations the 3D model may be modified, e.g., by segmenting components and/or reconstructing components using the processed 2D images. For example, the processed 2D images may include segmentation information that may be used to label, e.g., mesh points or facets on the 3D model. In some variations individual component portion of the subject's oral cavity (e.g., the teeth, individual teeth, the gingiva, etc.) may be reconstructed from the processed 2D images, e.g., using the 2D/3D projection engine 262.

Figure 2B:
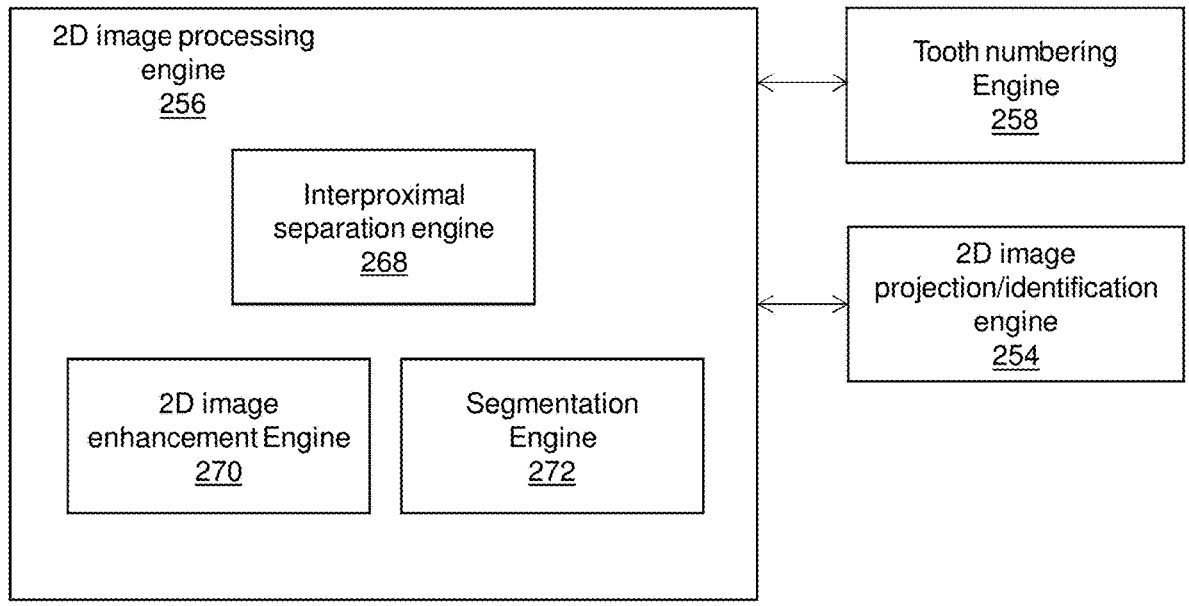
FIG. 2B schematically illustrates one example of a 2D image processing engine that may be part of a system for 3D modeling of a subject's oral cavity.

FIG. 2B shows an example of a schematic of a 2D image processing engine 256. In this example the 2D image processing engine 256 may be configured to identify and correct spacing between oral cavity components such as teeth, e.g., interproximal spacing. In other variations the 2D image processing engine may identify and/or correct other features from the oral cavity components, such as segmentation, gingival/tooth edges, etc. In FIG. 2B, the 2D image processing engine includes an interproximal separation engine 268 that may process identified 2D images (e.g., received by the 2D image processing engine from the 2D image projection/identification engine 254) to identify interproximal regions between individual teeth, including identifying planes between the teeth. These planes may be used to segment the teeth, e.g., by a segmentation engine 272. Alternatively or additionally, these planes may be used to enhance the 2D images to determine the separation between the dental components, e.g., using a 2D image enhancement engine 270 to enhance the 3D model.

Figure 2C:
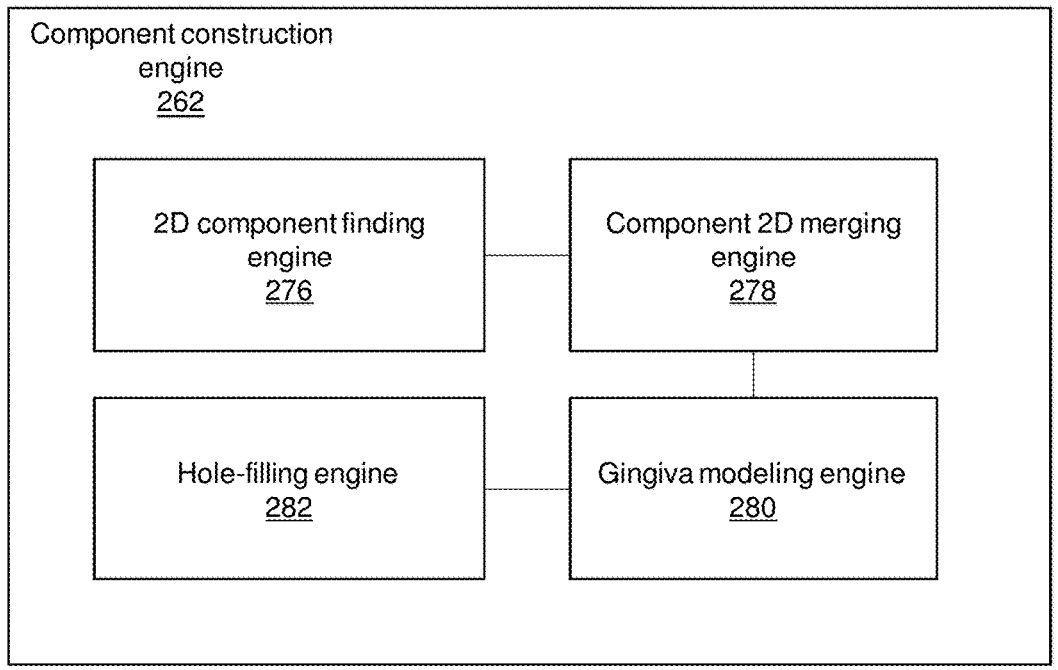
FIG. 2C schematically illustrates one example of a component construction engine portion of a system for 3D modeling of a subject's oral cavity.

FIG. 2C illustrates one example of a component construction engine 262 that may receive the processed 2D images. In some variations the component construction image may identify those (processed and/or unprocessed) 2D images that include a particular component, such as a particular tooth, e.g., using a 2D component finding engine 276. Once identified, the images of the components may be merged, using a Component 2D merging engine 278 to form one or more 3D component models. For example, the individual tooth components may be reconstructed from the processed 2D images in this way. In FIG. 2C, a gingival modeling engine 280 may also be included that may use the reconstructed tooth components to generate a separate gingival model, e.g., by subtracting the reconstructed teeth from the original 3D model and using a 3D processing engine, such as a hole-filling engine 282 to smoothly fill holes in the mesh of the gingival model. These 3D component parts may then be combined into a single, segmented, 3D model of the oral cavity. This model may be used as described below, e.g., to track tooth movement during treatment, to plan a treatment, to adjust a treatment, and/or to make or form an orthodontic appliance such as an aligner.

For example, a 3D model of the subject's oral cavity (e.g., dentition, gums, etc.) may be used to fabricate a dental appliance or a series of dental appliances. In some variations an apparatus such as those described herein be part of or may include an aligner fabrication engine (not shown). An aligner fabrication engine(s) may implement one or more automated agents configured to fabricate an aligner. Examples of an aligner are described in detail in U.S. Pat. No. 5,975,893, and in published PCT application WO 98/58596, which is herein incorporated by reference for all purposes. Systems of dental appliances employing technology described in U.S. Pat. No. 5,975,893 are commercially available from Align Technology, Inc., Santa Clara, Calif., under the tradename, Invisalign System. Throughout the description herein, the use of the terms "orthodontic aligner", "aligner", or "dental aligner" is synonymous with the use of the terms "appliance" and "dental appliance" in terms of dental applications. For purposes of clarity, embodiments are hereinafter described within the context of the use and application of appliances, and more specifically "dental appliances." The aligner fabrication engine(s) may be part of 3D printing systems, thermoforming systems, or some combination thereof.

Figure 2D:
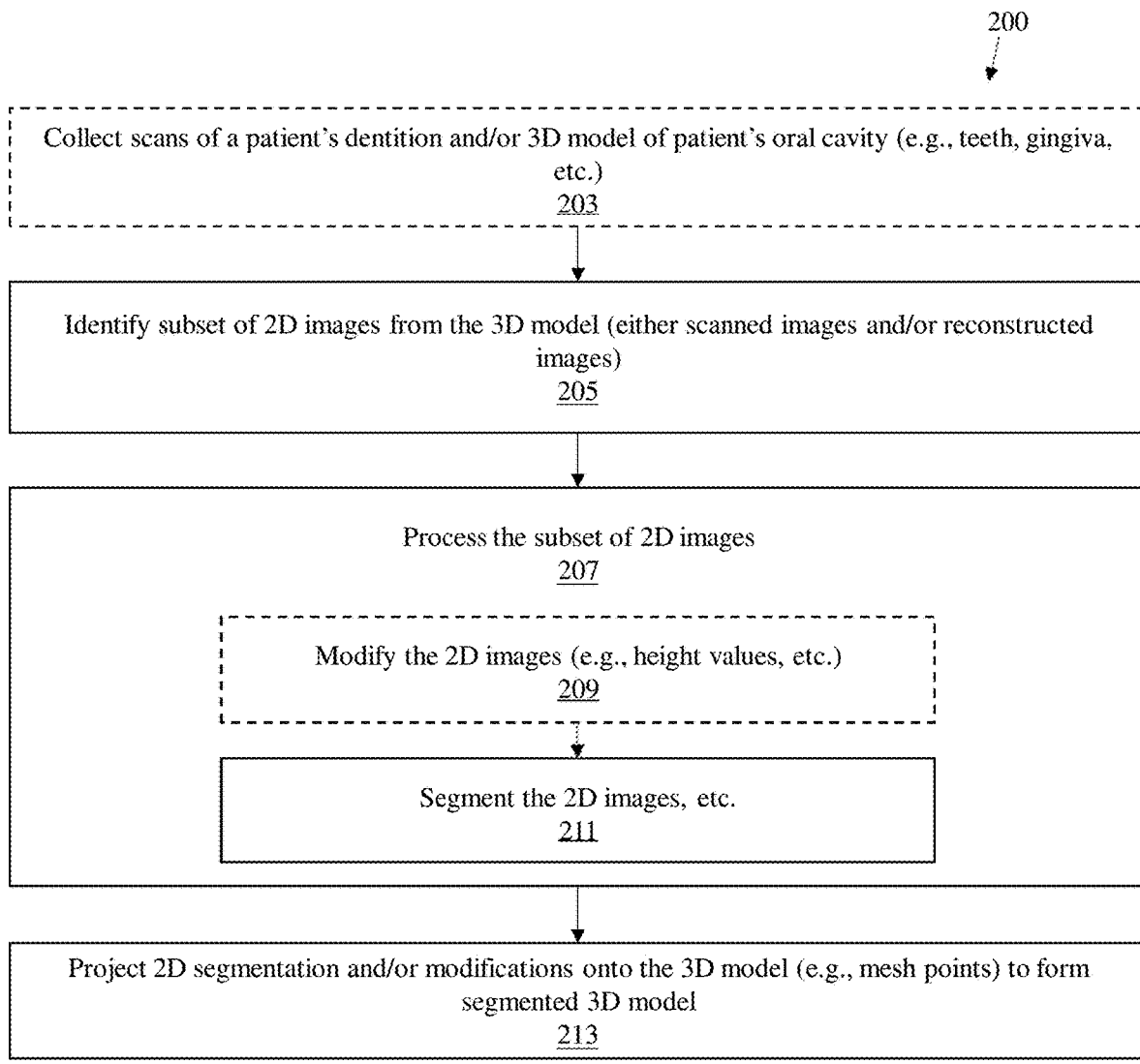
FIG. 2D illustrates one example of a method of segmenting a 3D model of a subject's oral cavity to identify component parts, such as individual teeth, gingiva, etc.

In use, a system such as illustrated above may be used to modify or improve a 3D model of a subject's oral cavity. FIG. 2D illustrate one example of a method of modifying a 3D model as described herein. In this example, the 3D model is modified by segmenting (e.g., providing segmentation values) the component parts. Similar steps may be used to modify a 3D by improving the quality of the 3D model.

In FIG. 2D, the method of segmenting a 3D model of a subject's oral cavity (e.g., into individual teeth, gingiva, etc.) may being by collecting a 3D model of the subject's oral cavity, which may include some or all of the teeth, gingiva, palate, tongue, etc. This 3D model may be referred to as an "original" or "unprocessed" 3D model; this original/unprocessed 3D model may be modified as described herein, and the modified 3D model may be referred to as a modified 3D model. Optionally, the method (and any apparatus configured to perform the method) may include collecting 2D scans of the subject's oral cavity. The scans may be correlated to the 3D model; in some variations the scans may be used to form the original 3D model. For example, an intraoral scanner may be used to scan the subject's oral cavity and generate the 3D model of the subject's teeth. As described, in any of the methods and apparatuses herein, the 2D images (e.g., scans) may be modified, e.g., by correcting, marking, etc., and these processed scans may be used to regenerate the 3D model and/or in some variations the processing done in the 2D scans, such as segmentation, may be mapped to the 3D model. Thus, as shown in FIG. 2D, a method may optionally include collecting scans (2D images) of a subject's dentition and/or 3D model of subject's oral cavity (e.g., teeth, gingiva, etc.) 203. In some variations collecting the 2D scans may include generating 2D sections, which may be taken through the 3D model. Although in FIG. 2D this step is shown as an initial step, alternatively or additionally, this step may be performed later, such as after an initial analysis of the 3D model (e.g., to identify tooth numbering, to identify occlusal lines, prior to segmenting, etc.).

Collected 2D images may then be analyzed to identify a subset of 2D images that include one or more features of the oral cavity to be processed, such as the teeth, gingiva, etc. 205. The identified 2D images, as mentioned, may be either or both scanned images and/or reconstructed images from the 3D model. The subset of images may be selected for inclusion into the subset based on a review of the content of the images, to determine if the one or more corresponding features are present in the images. For example, individual teeth may be separately and/or sequentially or iteratively examined and subsets of these images may be formed that include the tooth being examined at a particular time. The subset may include a minimum and/or maximum number of 2D images. In some variations a machine learning agent may be used to identify the one or more features from the 2D images. In some variations the teeth in the 3D model and/or 2D images may be pre-processed, for example, to number the teeth according to a standard dental numbering system. This preprocessing, such as numbering may be used to help quickly identify which 2D images have the selected feature(s). A method for determining tooth numbering may also include machine learning, in which the machine learning agent (e.g., a tooth numbering engine) may be trained to identify tooth number, as discussed above.

As mentioned, in some variations some or all of the 2D images may be generated as virtual sections through the original 3D model (or a modified version of the 3D model). The virtual sections may be taken so as to illustrate the one or more features.

The subset of 2D images may be processed 207. In some variations, processing may include (optionally) modifying the 2D images 209, such as indicating in some or all of the processed 2D images corrections to the 2D images. For example, corrections may include determining interproximal spacing, and/or correcting the interproximal spaces that may include, for example, scanning artifacts. Image processing may include segmenting the 2D images 211. Segmentation may be performed using a segmentation agent (or segmentation engine) that may apply one or more rules to determine the boundaries of each tooth, such as the boundaries between the teeth and/or the boundaries between the teeth and the gingiva, etc. In some variations the segmentation agent may be a machine-learning agent that is trained on one or more datasets to recognize boundaries between teeth or teeth and gingiva and to otherwise segment the teeth and/or gingiva. Segmentation may be performed on the 2D images and may be projected onto the 3D model (e.g., the original 3D model or an intermediate 3D model that is modified). In general, corrections or modifications of the 2D images may be translated to the 3D model, including by projecting onto the 3D model 213. For example, segmentation of teeth from the 2D images may be projected onto the 3D model; when the 3D model includes a mesh structure having a plurality of mesh points defining the structure, these mesh points may be labeled or otherwise marked to indicate that they are part of a particular structure e.g., may be segmented). The mesh may be modified so that the individual structures (e.g., teeth, gingiva, etc.) may be separate from each other (e.g., having separate mesh structures) that may share a common reference frame. The segmented teeth and/or gingiva may then be manipulated during later processing, such as when designing a treatment plan and/or forming orthodontic appliances based on a treatment plan.

In some implementations, the hole filling engine 282 may be used with 2D images constructed from planes between teeth where the 2D image represents the distance from the plane to the corresponding locations on the 3D mesh. In this instantiation, the hole filling engine 282 can be used to reconstruct portions of the 3D mesh where no mesh preexisted. For example, to reconstruct the mesial and distal mesh edges of teeth that could not be reconstructed by the intraoral scanner.

In variations in which machine learning is used, for example, to perform segmentation of the 2D images, conditional Generative Adversarial Network (cGAN) and/or other neural network can be used. For example, in some variations a segmentation engine may include a machine learning agent to segment one or more 2D images, or image-like inputs, into various relevant dental classes. Many dental classes can be predicted concurrently. Combining these predictions with knowledge of how the 2D inputs project onto the 3D mesh may allow for improved 3D segmentation, as described herein. Thus, machine learning approaches can be used to segment 2D inputs according to dental classes. The 2D machine learning predictions can be projected to a 3D mesh to classify each point (e.g., each point of the 3D mesh) and/or to modify the mesh. In some variations, classification of each point can be achieved by statistically combining the 2D images that support it (e.g., that include the feature(s) that is/are being segmented).

For example, a 3D model may be formed using 2D images collected with an intra-oral scanner. An intra oral scanner may work by moving the wand inside a subject's mouth to capture all viewpoints of every tooth. During scanning, the scanner may calculate distances to solid surfaces, e.g., from the wand (or the optics doing the scanning). These distances may be recorded as images called 'height maps'. Each height map may be overlapped algorithmically, or 'stitched', with the previous set of height maps to generate a growing 3D model. As such, each 2D image may be associated with a rotation in space, or a projection, to how it fits into the 3D model. After scanning, the final model may include a set of 3D points and their connections with each other (i.e. a mesh).

The apparatuses (including software) described herein may operate on the mesh, and also on the 2D input images that are used to construct the mesh, to (among other things) segment points into relevant dental classes, such as tooth, gingiva or moving tissue (tongue, fingers, etc.). As will be described in greater detail below, this labeled mesh may establish the basis of treatment planning for both orthodontic and restorative cases.

Figures 3A, 3B, 3C:
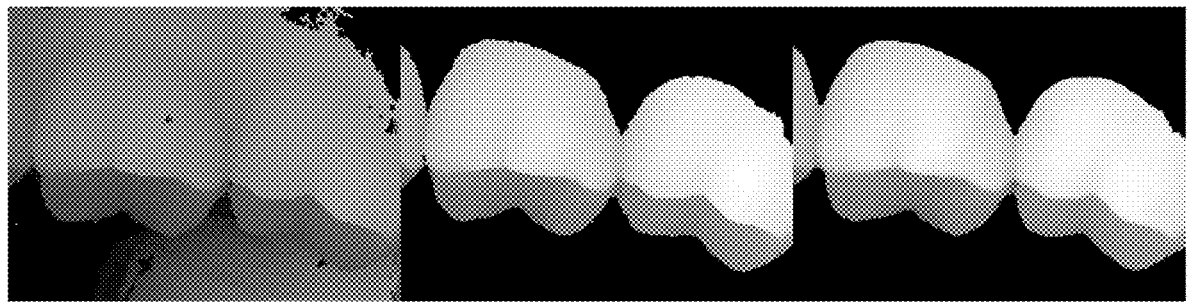
FIGS. 3A-3C illustrate training an agent, e.g., a machine learning agent, to recognize individual teeth from images of a subject's teeth.

Accurate mesh segmentation may be important for treatment planning. As mentioned, the segmentation engine may use machine learning to segment the 2D images into their relevant dental classes described herein. A conditional generative adversarial (cGAN) and/or other neural network may be used for segmentation, to learn how to map height map inputs (an example of which is shown in FIG. 3A) to a set of human labeled segmented images (e.g., FIG. 3B). The set can comprise several, hundreds, thousands, millions, etc. of human labeled segmented images. The result of this training may be a function that can predict labels directly from height maps. Labels can be binary, many valued, with each value corresponding to a different class, or they may be continuously valued (such as a target height map). FIGS. 3A-3C illustrate identifying teeth height maps from input height map images. FIG. 3C shows an example of a cGAN output.

Figure 4A:
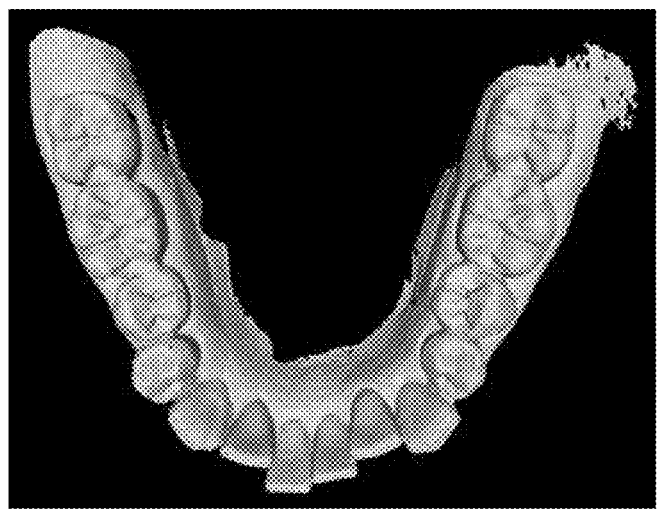
FIG. 4A is an example of a 2D projection of an occlusive view of a raw 3D model.
Figure 4B:
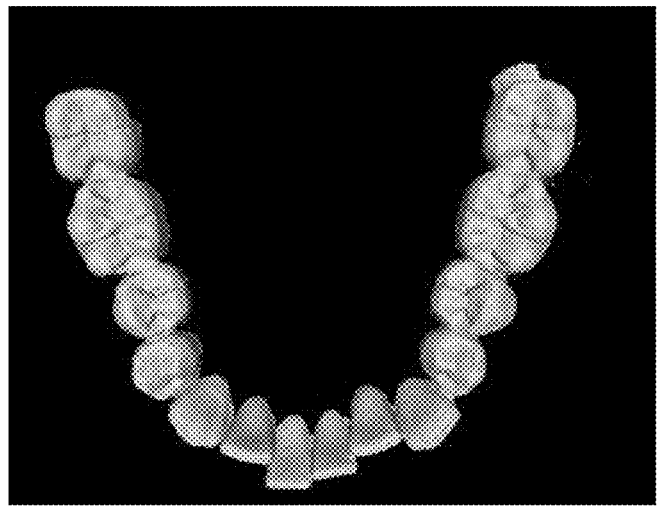
FIG. 4B shows the example projection of FIG. 4A after analyzing and labeling the 2D image of FIG. 4A (and others) and applying this analysis and labeling to a 3D model of the subject's dentition.

Because the inputs may each be associated with a projection onto the mesh, machine learning outputs can each be mapped to the appropriate points in the mesh. As such, each point in the mesh has support from one or more 2D predictions. In some variations, conflicts in point labels between the supporting 2D predictions can be resolved statistically, such as taking a consensus or using Bayes rule. An example of a raw 3D model, projected to 2D from above is shown in FIG. 4A. In this example, the 3D model may be segmented by applying a segmentation engine that uses machine learning to process the 2D images making up this mesh (or a subset thereof) and using resulting tooth segmentation predictions to label the 3D points (and remove non-tooth points); this is illustrated in FIG. 4B.

In some variations, points of the 3D model may be labeled (to indicate segmentation and/or other corrections, modifications or results of processing) when there are multiple 2D images using a technique such as Bayes rule. For example, if there are calluses of only teeth (T) and other (O), the model may predict that each pixel is either positive (P) or negative (N) for teeth (or for a specific tooth number). Using a test set, one may calculate:

$$P(T|L) = \frac{P(L|T) \cdot P(T)}{\sum_{c}^{T,N} P(L|C) \cdot P(C)}$$

A scanner, such as an intraoral scanner, may capture other information in addition to height maps. This other information, corresponding to one or more properties of the scanned structure (e.g., teeth, gingiva, etc.) may include, e.g., color inputs from a camera (textures), recordings of scanning quality, and counts of how many raw scans contributing to each height map pixel. These inputs may be combined in any combination and/or may be used jointly to predict dental classes by the segmentation engine (e.g., using machine learning) and/or may be included in the 3D model. An example of using these inputs is below. The inputs may include a height map, such as is shown in FIG. 5A, a count map (an example of which is shown in FIG. 5B), a grades map (an example of which is shown in FIG. 5C), and a texture for the image (an example of which is shown in FIG. 5D). FIG. 5E shows the target label (in this case 'empty space') and FIG. 5F shows a prediction from a machine learning engine trained with these inputs and targets, differentiating between empty and non-empty space (black and white).

Figures 6A, 6B:
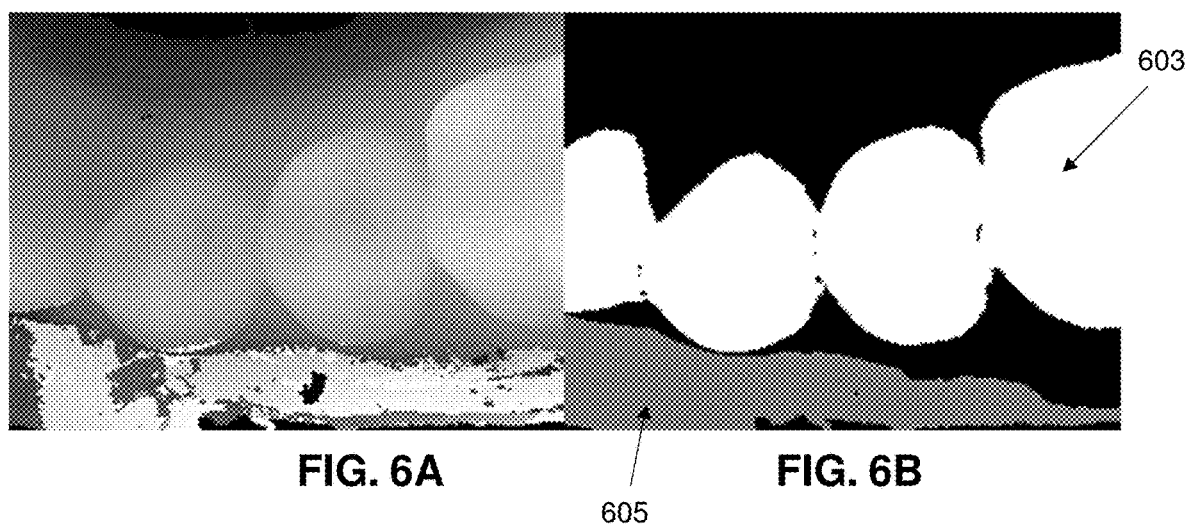
FIGS. 6A-6B illustrate segmentation prediction based on a height map (shown in FIG. 6A), which may be used to differentiate between tooth (shown in white) and non-tooth (e.g., gingiva and excess materials in black and gray, respectively).

The methods and apparatuses described herein may be used, for example, to segment multiple labels at the same time (e.g., concurrently and/or sequentially). For example, machine learning outputs may be used to predict many labels simultaneously. In some variations, a different output channel may be used for each label. For example, a three-channel RGB image may be generated with each dental label having a different color. An example of this is shown in FIGS. 6A-6B. FIG. 6A shows a height map input on the left, and the segmented image is shown in FIG. 6B. In this example, the teeth are labeled as white 603, and excess material ("non-teeth") are shown labeled as grey (may be shown in a color, such as red) 605. An entire subset of 2D images may be analyzed in this manner and the results may be combined to form a consensus (e.g., using Bayes rule or a comparable technique to distinguish between conflicting regions) that may be applied to the 3D model.

Figure 7:
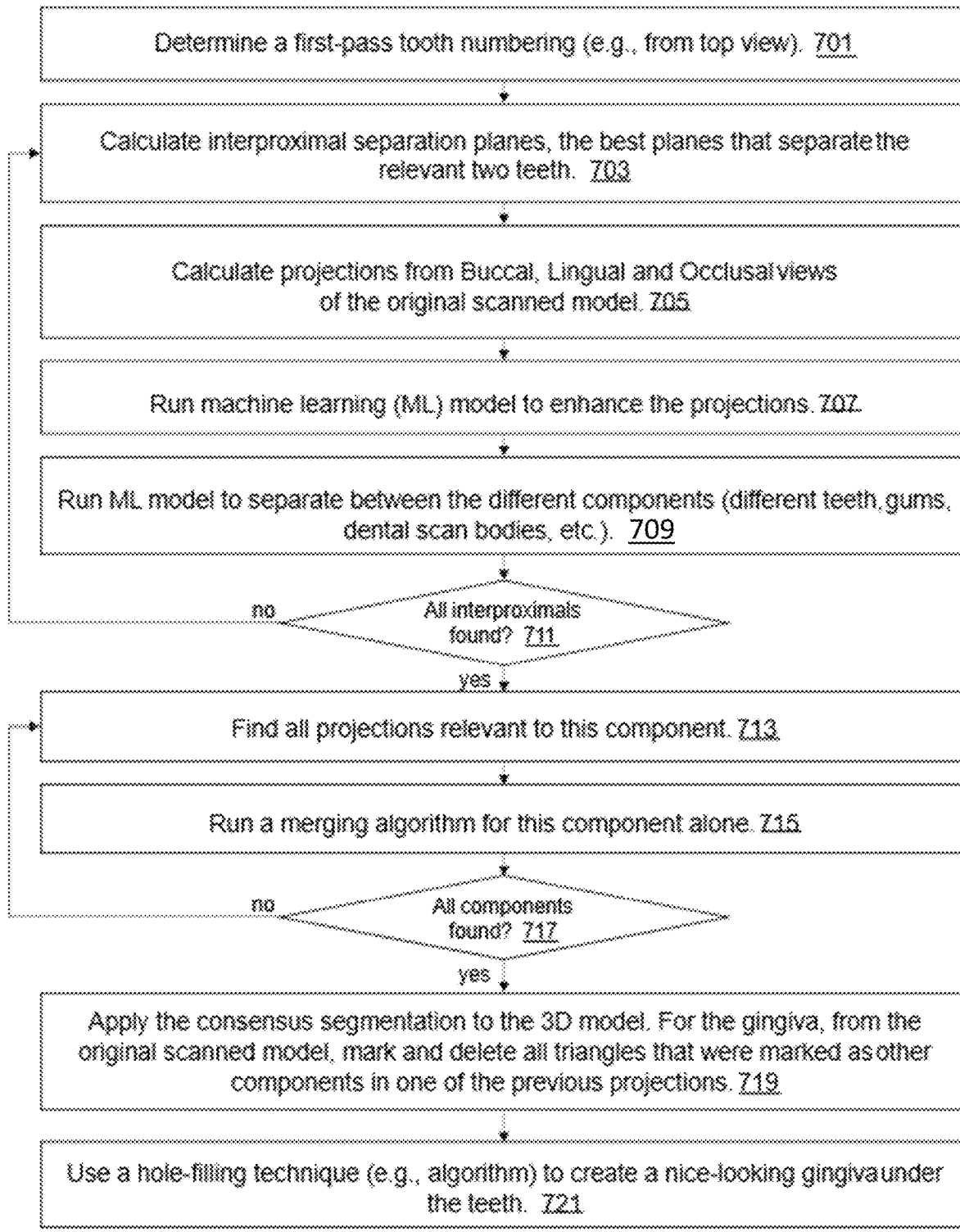
FIG. 7 illustrates one example of a method of forming a segmented 3D model of a subject's oral cavity that includes separately and specifically identified component parts (e.g., individual teeth, gingiva, etc.).

FIG. 7 illustrates one example of a method for segmenting a 3D model of a subject's oral cavity (e.g., teeth, gingiva, etc.) as described herein. Methods and apparatuses as described herein may be used to segment a 3D model so that it may be separated, e.g., digitally, into various components. The components may be the individual teeth, the gums, implants, restorative tooth preparations, and other structures within the subject's oral cavity.

In the variation shown in FIG. 7, interproximal spacing, e.g., the spacing between teeth, may be used to identify the boundaries between teeth. For example, in some variations the apparatus may include identifying interproximals and calculating directions to view the 3D model in order to optimally see the interproximal space. The views that best (e.g., maximally) show the interproximal spacing between two or more teeth may be used to generate slices (e.g., 2D images, as described above) that may in turn be processed as described above; alternatively, the actual collected 2D images corresponding to these maximal views may be identified from the set of scan images and used.

For example, 2D height map projections may be used, and these 2D height map projections may be improved, and these interproximal height map projection images may be improved to better-represent the interproximal regions. Thus, in some variations, the height map of different components shown in the 2D images may be used to segment the components, such as differentiating between a left tooth, right tooth, gingiva, air etc.

A selected component, such as a particular tooth, may be located in the improved height map projection images and these 2D images may be refined so to form improved height map projection images that include only the selected component. These improved projections may then be combined using a merge algorithm, such as marching cubes, to construct the selected component.

Figure 10A:
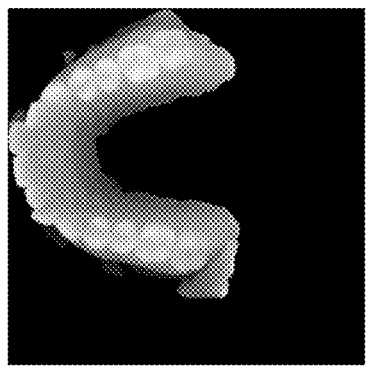
FIGS. 10A-10C illustrate the steps of FIG. 9, showing a height map (FIG. 10A), ordering the teeth in the image (FIG. 10B), and determining a probably tooth numbering order from the height map information (FIG. 10C).
Figure 10B:
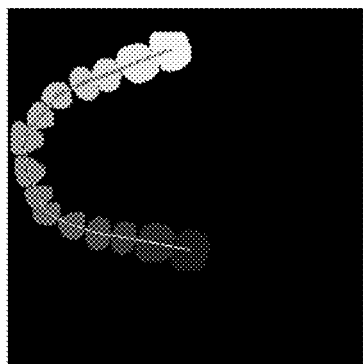
Figure 10C:
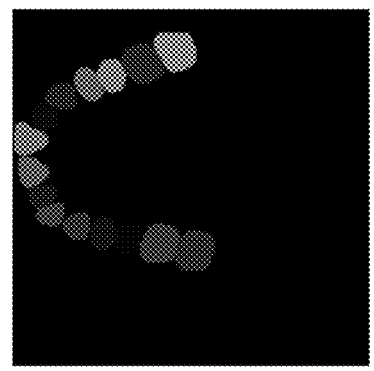

The procedure shown in FIG. 7 may be a special case of the method illustrated and described above in FIG. 2D. In FIG. 7, a digital 3D model of a subject's teeth may be received and and/or generated (e.g., from a set of 2D images and/or height maps). In some variations the 3D model and/or 2D images corresponding to the 3D model may be analyzed to determine an initial tooth numbering (this initial tooth numbering may be corrected or refined later) 701. For example, a top (e.g., occlusal) view of the teeth may be used to generate tooth numbering. The tooth numbering may be optional, but may be particularly helpful in the later steps. FIGS. 8A-8B illustrate one example of tooth numbering. In FIG. 8A, the top view, which may correspond to an actual top view, e.g., taken from a single or composite scanned 2D image, and/or from a projection of the 3D model) may be analyzed, e.g., by a tooth numbering engine, to determine the tooth numbering, as shown in FIG. 8B, in which individual teeth are numbered according to a standardized numbering scheme. FIG. 9 illustrates one example of a method of numbering the teeth, which may be automatic or semi-automatic. In FIG. 9, a height map may be used to first separate each tooth as a separate instance; tooth numbering may be calculated at the same time by calculating tooth numbering probabilities for each instance 901 (see, e.g., FIG. 10A). For example, jaw ordering may be assigned to all tooth instances, for example, using a technique such as a Held-Karp algorithm for the traveling salesman problem 903 (see, e.g., FIG. 10B). A maximum likelihood estimate of all tooth probabilities jointly across the jaw may be determined, this maximum likelihood may preserve the dental ordering (e.g., molar→premolar→canine, etc.) 905. See, e.g., FIG. 10C.

Figure 11A:
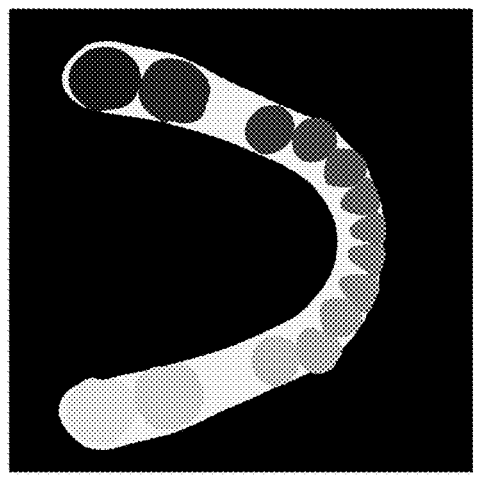
FIGS. 11A-11B illustrate one variation in which interproximal spacing is identified in a plurality of 2D slices or images of the subject's teeth, and (as shown in FIG. 11B) planes showing most likely interproximal separation between adjacent teeth.
Figure 11B:
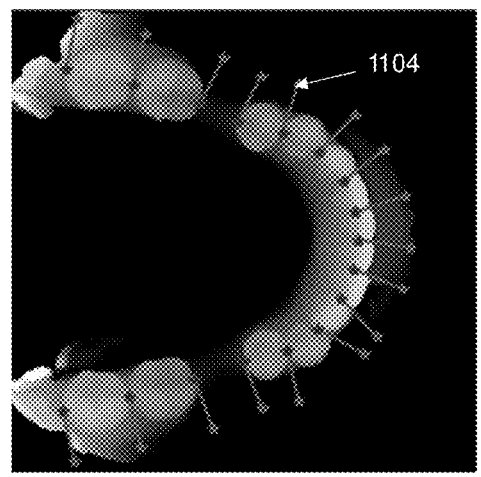

Returning to FIG. 7, once the (optional) tooth numbering has been performed, and may be recorded in the 3D model or associated data about the 3D model, the method may include iteratively identifying the interproximal spacing between the teeth, including identifying a plane that maximizes the views of the interproximal region between the teeth. For example, the method (or an apparatus configured to perform it) may calculate interproximal separation planes, e.g., the best planes that separate the relevant two teeth 703. An example of this is illustrated in FIGS. 11A-11B. In FIG. 11A, for every interproximal space found, the method or apparatus may calculate separation planes, which are the "best" planes that separate the relevant two teeth. A plane perpendicular to these planes/lines 1104 may provide a view of the teeth that maximally shows the interproximal region. Thus, as shown in FIG. 7, the projections from buccal, lingual and occlusal views may be determined based on these interproximal planes/lines from the original 3D model 705. As mentioned above, alternatively or additionally, actual scanned 2D images corresponding to the projections may be used.

Figure 12A:
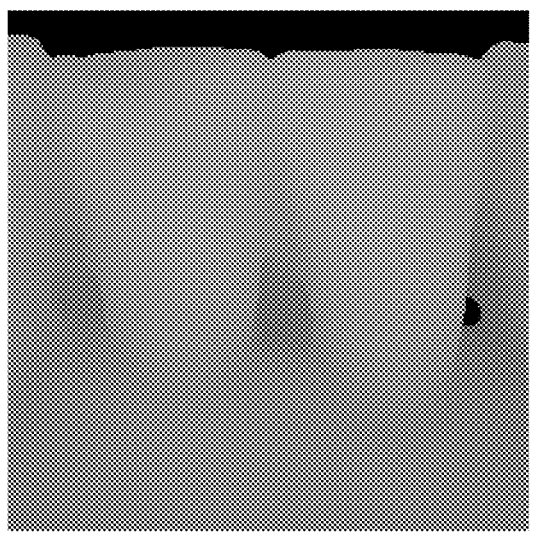
FIGS. 12A-12C show one variation of a method of segmenting a subject's teeth in which 2D projections and/or captured images are identified, such as projections from buccal (FIG. 12A), lingual (FIG. 12B) and occlusal (FIG. 12C) views taken from the original (unsegmented and unmodified) 3D model.
Figure 12B:
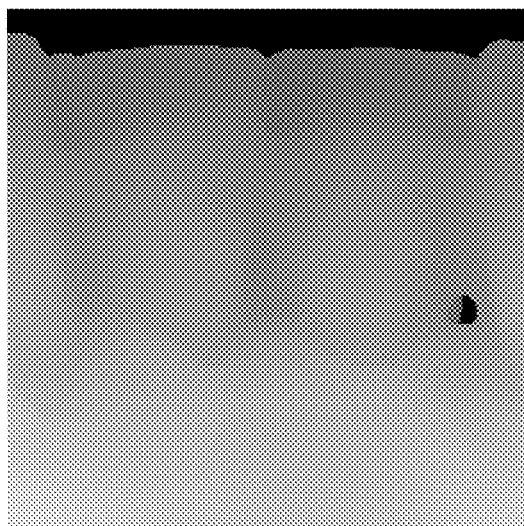
Figure 12C:
Figure 15A:
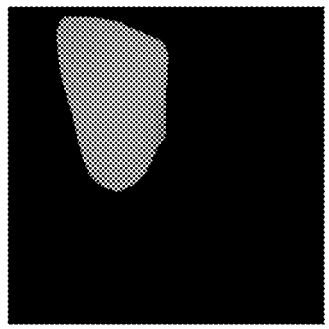
FIG. 15A-15F illustrate identifying different 2D views of a same component (e.g., tooth) across multiple 2D views, projections or captured images.
Figure 15B:
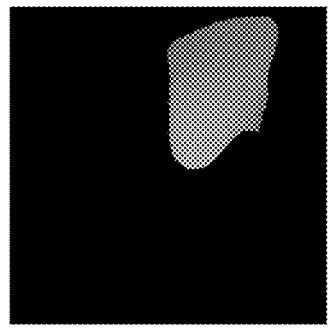
Figure 15C:
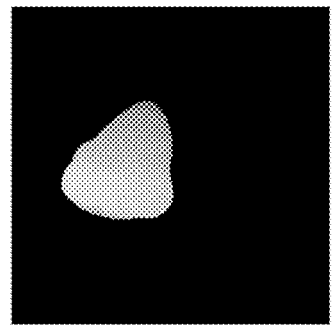
Figure 15D:
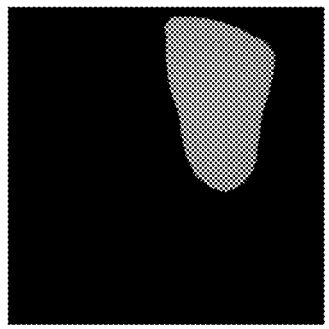
Figure 15E:
Figure 15F:
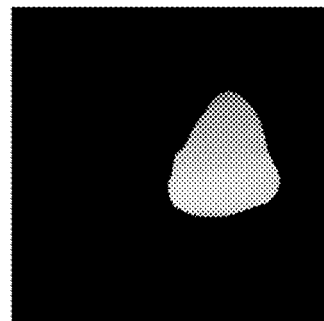

The buccal, lingual and/or occlusal views identified as perpendicular to the interproximal plane may be enhanced 707. In some variations machine learning may be used to enhance the projections. For example, as shown in FIGS. 12A-12C illustrate buccal (FIG. 12A), lingual (FIG. 12B) and occlusal (FIG. 12C) projections through the original 3D model based on the interproximal plane calculated from the 3D model. These views may be enhanced, as shown in FIGS. 13A-13B. FIG. 13A shows the same view as in FIG. 12A before enhancement of the interproximal region. FIG. 13B shows the same view after enhancement of the interproximal region; as shown, the interproxial regions 1305 between the teeth have been enhanced and enlarged to correct for artifacts from the scanning. In FIG. 13B, this may be done by trained network (e.g., using machine learning).

The same views, and/or additional views, may also be processed in other ways as well, including to determine the boundaries between the different structures, for segmentation. For example, FIGS. 14A-14B illustrate the detection of segmentation boundaries in an enhanced image (FIG. 14A shows the enhanced image of FIG. 13B). In FIG. 14B the segmentation engine, which may include a trained machine-learning agent, has detected different teeth, gums, dental scan bodies, etc. In this example, they are each indicated by a different color. Returning to FIG. 7, the method may include segmenting the 2D images, e.g., by a trained network, into different components, such as different teeth, gums, dental scan bodies, etc.) 709.

This process of calculating the interproximal planes, identifying 2D images perpendicular to the planes, enhancing these 2D images and/or segmenting them may be repeated 711 until all of the interproximal planes are identified and processed. All of the processed 2D images (e.g., projections) may be collected together.

Figure 16:
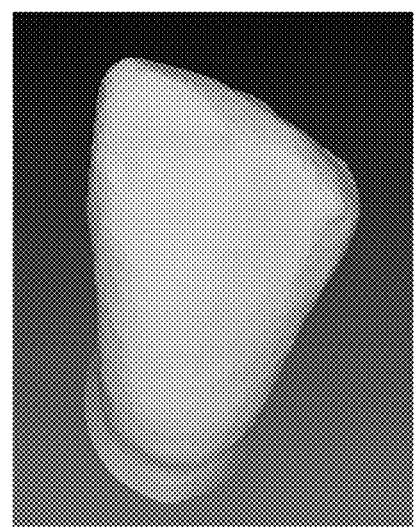
FIG. 16 illustrate a combined or merged image based on the multiple different 2D views such as shown in FIGS. 15A-15F.

Thereafter, individual components may be reconstructed from the processed 2D images. For example, the method may collect all of the processed 2D images that show a particular component 713, and may run a merging algorithm for this component (which may resolve conflicts between different images as described above, and may combine them into a single reconstructed element 715. This is illustrated in FIGS. 15A-15F, showing a plurality of identified images including a particular element or component, shown here as a tooth. These images may be merged into a single representation of the particular element, as shown in FIG. 16.

Figure 17A:
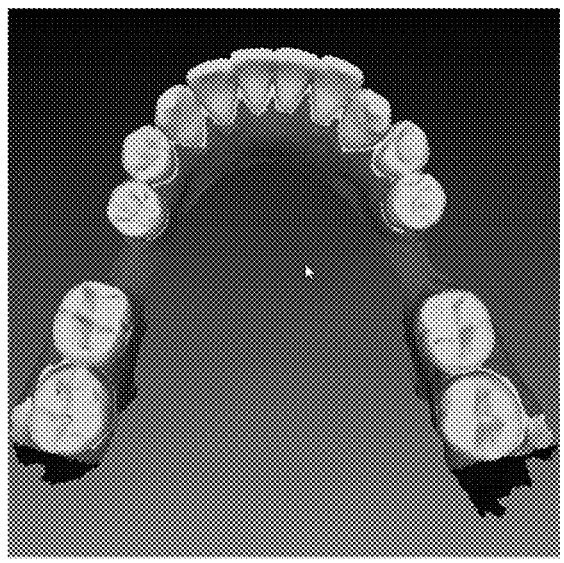
FIGS. 17A-17B illustrate modeling of the gingiva following segmentation of the teeth.
Figure 17B:
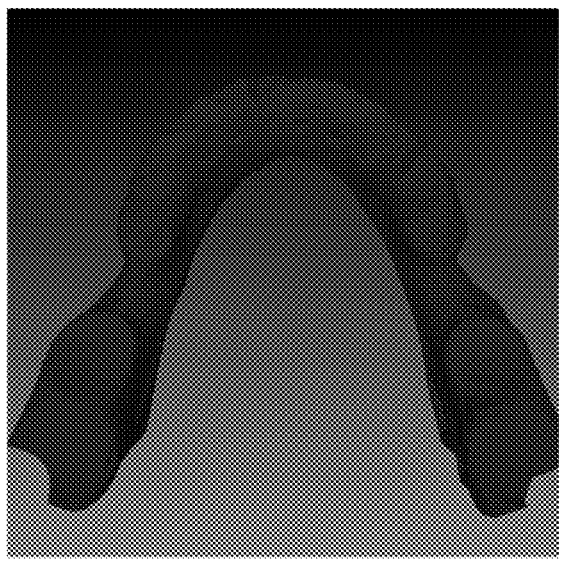
Figure 18:
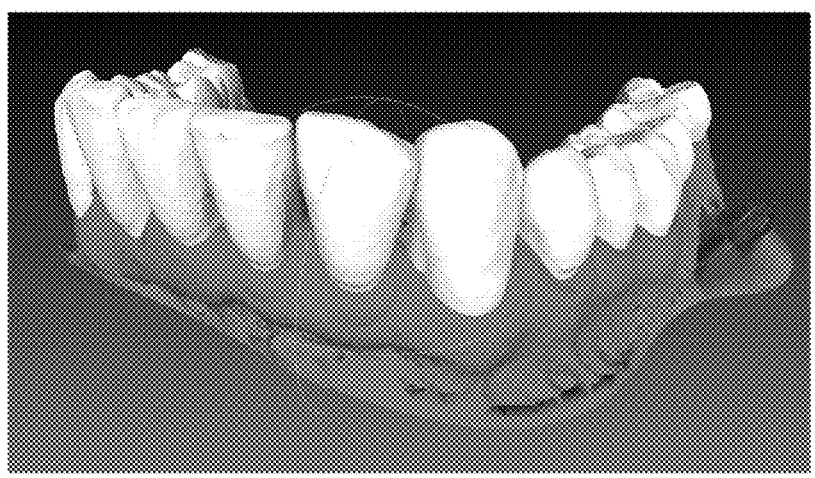
FIG. 18 shows a completely segmented and/or corrected 3D model formed as described herein.

The gingiva may be similarly reconstructed; in some variations, the gingiva may be segmented by subtracting the reconstructed teeth from the rest of the 3D model, which is primarily the gingiva. As described in FIG. 7, the original scanned model may be modified by the reconstructed teeth from the earlier steps 719. For example, in the original 3D model mesh representation of the 3D model may be modified by removing (e.g., marking for deletion then deleting) all triangles or points that were indicated to be part of one or more of the other elements from the 2D images, e.g., projections. Any holes or discontinuities that are identified may be filled using a filling procedure to provide a final smooth gingiva that underlies the teeth 721. This is illustrated in FIGS. 17A-17B. FIG. 17A shows the 3D model with the segmented teeth; FIG. 17B shows the segmented model with the teeth removed, representing just the gingiva. Finally, all of the segmented components may be combined, as shown in FIG. 18.

In general, these methods may allow for improving of interproximal space accuracy, and for assisting detection of interproximal carries. The improved 3D images may also be useful for, in general, creating better rendering and/or coloring of the tooth, e.g., by different material reflection parameters to tooth and gum. As mentioned above, better 3D models, and in particular, better segmented 3D models, may permit much better treatment plan, and fabrication of more accurate orthodontic appliances, including better die separation.

For example, the methods and apparatuses described herein may allow the input of just an initial 3D model, and may refine this model. As mentioned above, 2D projections through the 3D model may be used for processing to improve the 3D model. Thus there may be no need for intermediate data from, e.g., a scanner.

In some variations, the output of the apparatus and methods described herein when used to segment the 3D model may result in a 3D model that is segmented into the composite parts, and may be readily separated into component digital models of the different components. When interproximal spacing is used, as described in FIG. 7, above, the closed interproximal spaces on the 3D model may be opened up.

Thus, these methods and apparatuses may include multiple sources of information that may be incorporated into model inputs and used jointly for prediction. Multiple dental classes can be predicted concurrently for a single model or models. In addition, the accuracy may be higher than traditional image and signal processing approaches.

FIG. 20 illustrates one example of a method as described herein. This method may be performed by a processor, coupled with or in communication with a scanner (e.g., an intra-oral scanner) or may otherwise receive scan data on a patient's dentition, or from a model of the patient's dentition. In FIG. 20, the method includes accessing a plurality of first two-dimensional (2D) images 2001, wherein the plurality of first 2D images: represents a subject's oral cavity, each has first areas that can be segmented into a plurality of dental classes, each has a first relationship to a first three-dimensional (3D) model of the subject's oral cavity, and each has first height map data representing distances between the subject's oral cavity and an image capture device. In some variations, the method may also include accessing one or more automated machine learning agents trained to modify one or more second 3D models into the plurality of dental classes 1003. The trained modifications may use second height map data of a plurality of second 2D images and further using second relationships between the plurality of second 2D images and the one or more second 3D models. The method may further include instructing the one or more automated machine learning agents to use the first height map data to modify the first areas of the plurality of first 2D images to get a plurality of modified first 2D images 2005. In some variations the method may also include using the first relationships and the plurality of modified first 2D images to modify first mesh regions of the first 3D model corresponding to the first areas of the plurality of first 2D images 2007.

In some variations, the method may also include gathering the plurality of second 2D images from a training datastore. The method may also include identifying one or more modifications to second areas of the plurality of second 2D images, and/or training the one or more automated machine learning to use the second height map data to provide the one or more modifications to the second areas of the plurality of second 2D images to get a plurality of modified second 2D images. The method may also include training the one or more automated machine learning to use the second relationships and the plurality of modified second 2D images to modify second mesh regions of the one or more second 3D models corresponding to the second areas.

These improvements in 3D model rendering and segmentation may therefore provide 3D shapes and 3D shapes with color that may improve the analysis of the subject's oral cavity and treatment planning. For example, the improved 3D models resulting from the methods and apparatuses described herein may provide a 3D shape and/or color that is sufficiently segmented to allow more accurate modeling and formation of tooth accessories including artificial teeth, veneers, fillings, etc. The 3D models described herein may include accurate colors, including scanned colors and may improve the color properties, such as reflectivity, etc. The optical properties of the non-tooth components, such as gums and palate may also be accurately rendered. Transparency, particularly for incisory teeth, may also be determined and/or modeled.

Any of the methods and apparatuses described herein may be used on a completed scan, on a non-final scan, and/or while the teeth are actively being scanned. For example, in some variations, the methods and apparatuses described herein may be used to provide feedback to a user that is scanning or that may go back to re-scan or continue scanning the subject's teeth. Thus, these methods may indicate when there are incomplete or poorly-represented regions of the teeth, e.g., identifying holes or gaps in teeth or between teeth and gums. For example, the apparatus or methods may include telling the user to complete a scan of a particular region of the oral cavity (e.g., to re-scan tooth number 13, etc.).

Additional advantages of these methods and apparatuses may include improving the 3D shapes, restorative treatments, and diagnostics. For example, dental and orthodontic treatments may be improved by knowing the accurate identity and morphology of each tooth and the ability to provide treatment to specific teeth, using information specific to each tooth type. For example, these methods and apparatuses, and the resulting improved 3D models, may also allow for improve soft-tissue detection and access material, including identifying the boundaries between teeth, which may also help improve inter-proximal spacing. In some variations the teeth may be rescanned successive 3D models made over time to more accurately track tooth movement, cavities, gum recession, etc.

The methods and apparatuses described herein may also improve restorative treatments. For example, the improved 3D models, which may include accurate color, reflectivity, and transparency of the teeth may be used to show the effects of treatments such as tooth whitening, veneers, etc. in a more accurate manner. In some variations these methods may allow the teeth to identify incisors (e.g., showing veneer treatments), etc. The improved 3D models may also be used to help define, display and examine treatments such as displaying crown shapes, etc. The accurate tooth numbering and modeling may also assist in automatically generating and/or selecting treatment plans.

In addition, diagnostics may be improved by the methods and apparatuses described herein. For example, these methods and apparatuses may be useful to help with gum recession (e.g., gum recession diagnostics, including looking at longitudinal data, e.g., date over time), and generally looking at changes in the subject's oral cavity over time, including both global and regions changes. This may allow and support improved progress tracking, which may be part of a scanner (e.g., intraoral scanner) system that may include this functionality. Thus, these methods and apparatuses may be used to diagnose tooth wear, and the improved segmentation in particular may enhance the ability so see changes in the teeth over time. In addition, the enhanced correlation with the 2D images, and in particular the 2D images taken from the scan data may be use useful for following and measuring surface features on the teeth such as plaque accumulation.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-implemented method comprising:
identifying a plurality of two-dimensional (2D) images of a subject's oral cavity, wherein the plurality of 2D images each comprise height map data corresponding to a distance between an image capture device and at least a portion of the subject's oral cavity, and the plurality of 2D images are each associated with one or more projection values to relate the each 2D image to a digital three-dimensional (3D) model of the subject's oral cavity;
processing the plurality of 2D images to segment each 2D image of the plurality of 2D images into a plurality of dental classes; and
using the one or more projection values of each 2D image of the plurality of 2D images to project the segmented 2D images onto the 3D model to segment the 3D model into a segmented 3D model into the plurality of dental classes.

2. The computer-implemented method of claim 1, further comprising collecting the plurality of 2D images and the height map data of each of the plurality of 2D images with an intraoral scanner.

3. The computer-implemented method of claim 1, further comprising collecting the plurality of 2D images by identifying a view of the 3D model and generating a 2D projection of the 3D model from the view.

4. The computer-implemented method of claim 1, further comprising collecting the plurality of 2D images and the height map data of each of the plurality of 2D images from scanned images of the subject's oral cavity.

5. The computer-implemented method of claim 1, further comprising modifying the 2D images.

6. The computer-implemented method of claim 5, wherein modifying comprises adjusting the height map data of each 2D image.

7. The computer-implemented method of claim 1, wherein processing the plurality of 2D images comprises applying a trained machine-learning agent to segment each of the 2D images.

8. The computer-implemented method of claim 7, wherein processing comprises using a conditional Generative Adversarial Network.

9. The computer-implemented method of claim 1, wherein projecting the segmented 2D images onto the 3D model comprises resolving conflicts between the segmentation of each 2D image prior to projecting onto the 3D model.

10. The computer-implemented method of claim 9, wherein resolving the conflicts comprises applying Bayes' Theorem, deconflicting the conflicts through voting, or some combination thereof.

11. The computer-implemented method of claim 1, wherein the one or more projection values of each of the plurality of 2D images represents a projection of pixels on the each of the plurality of 2D images to a face or vertex of a mesh of the 3D model.

12. The computer-implemented method of claim 1, wherein using the one or more projection values of each 2D image of the plurality of 2D images to project the segmented 2D images onto the 3D model comprises mapping one or more pixel values from pixels of the segmented 2D images onto one or more faces of a mesh of the 3D model.

13. The computer-implemented method of claim 1, wherein the plurality of dental classes comprise teeth, gums, and excess materials.

14. A system comprising:
one or more processors;
a memory coupled to the one or more processors, the memory configured to store computer-program instructions, that, when executed by the one or more processors, perform a computer-implemented method comprising:
identifying a plurality of two-dimensional (2D) images of a subject's oral cavity, wherein the 2D images correspond to a digital three-dimensional (3D) model of the subject's oral cavity;
processing the plurality of 2D images to segment each 2D image into a plurality of different structures; and
projecting the segmented 2D images onto the 3D model to form a segmented 3D model.

15. The system of claim 14, wherein the computer-implemented method further comprises: collecting the plurality of 2D images by identifying a view of the 3D model and generating a 2D projection of the 3D model from the view.

16. The system of claim 14, wherein the computer-implemented method further comprises: collecting the plurality of 2D images from scanned images of the subject's oral cavity.

17. The system of claim 14, wherein the computer-implemented method further comprises: modifying the 2D images.

18. The system of claim 17, wherein the computer-implemented method further comprises modifying the 2D images by adjusting a height map of each 2D image.

19. The system of claim 14, wherein the computer-implemented method further comprises: processing the plurality of 2D images by applying a trained machine-learning agent to segment each of the 2D images.

20. The system of claim 14, wherein the computer-implemented method further comprises: processing using a conditional Generative Adversarial Network or other Neural Network.

21. The system of claim 14, wherein the computer-implemented method comprises projecting the segmented 2D images onto the 3D model by resolving conflicts between the segmentation of each 2D image prior to projecting onto the 3D model.

22. The system of claim 21, wherein the computer-implemented method further comprises: resolving the conflicts by applying Bayes' Theorem.

* * * * *